United States Patent

Bruna et al.

Patent Number: 5,447,151
Date of Patent: Sep. 5, 1995

[54] POWDER INHALER WITH SUCTION ACTUATED LOCKING MEANS

[75] Inventors: Pascal Bruna, Rouen; Michel Brunet, Sainte-Colombe-La-Commanderie, both of France

[73] Assignee: Valois, Le Neubourg, France

[21] Appl. No.: 39,061

[22] PCT Filed: Oct. 4, 1991

[86] PCT No.: PCT/FR91/00777
   § 371 Date: Apr. 2, 1993
   § 102(e) Date: Apr. 2, 1993

[87] PCT Pub. No.: WO92/05823
   PCT Pub. Date: Apr. 16, 1992
   (Under 37 CFR 1.47)

[30] Foreign Application Priority Data
   Oct. 4, 1990 [FR] France .................. 90 12263

[51] Int. Cl.[6] .......... A61M 15/00; A61M 16/00; B05D 7/14; B65D 83/06
[52] U.S. Cl. ............. 128/203.15; 128/203.19
[58] Field of Search .......... 128/203.15, 203.12, 128/200.14, 203.21, 203.19

[56] References Cited

U.S. PATENT DOCUMENTS

| | | |
|---|---|---|
| 2,581,182 | 1/1952 | Fields . |
| 2,587,215 | 2/1952 | Priestly ................. 128/203.15 |
| 4,524,769 | 6/1985 | Wetterlin . |
| 4,570,630 | 2/1986 | Elliott et al. ............. 128/203.15 |
| 4,627,432 | 12/1986 | Newell et al. . |
| 4,811,731 | 3/1989 | Newell et al. . |
| 4,907,583 | 3/1990 | Wetterlin et al. ........... 128/203.15 |
| 5,004,021 | 4/1991 | Ulyanitsky et al. .......... 128/203.15 |
| 5,031,610 | 7/1991 | Armstrong et al. .......... 128/203.15 |
| 5,113,855 | 5/1992 | Newhouse ............... 128/203.15 |

FOREIGN PATENT DOCUMENTS

| | | |
|---|---|---|
| 0069715 | 1/1983 | European Pat. Off. ....... 128/203.15 |
| 0079478 | 5/1983 | European Pat. Off. . |
| 0166294 | 10/1989 | European Pat. Off. . |
| 2334424 | 7/1977 | France . |
| 2041763 | 9/1980 | United Kingdom . |
| 2165159 | 4/1986 | United Kingdom .......... 128/203.15 |
| 628931 | 10/1978 | U.S.S.R. ................ 128/203.15 |
| 1503827 | 8/1989 | U.S.S.R. ................ 128/203.15 |
| 1577796 | 7/1990 | U.S.S.R. ................ 128/203.15 |
| 9007351 | 7/1990 | WIPO .................. 128/203.15 |
| 9013328 | 11/1990 | WIPO . |

*Primary Examiner*—Kimberly L. Asher
*Attorney, Agent, or Firm*—Sughrue, Mion, Zinn, Macpeak and Seas

[57] ABSTRACT

A powder inhaler comprising a box (1) in which a suction channel (84) is formed enabling a user to inhale a powder, the inhaler being characterized in that it includes a pusher (2) associated with a return spring (83), actuation thereof enabling a dose of powder to be brought into a position enabling it to be sucked into the suction channel (84), and in that the box (1) includes a locking mechanism enabling the pusher (2) to be locked after it has been actuated, and enabling it to be unlocked when the user sucks up the dose of powder in the channel (84).

36 Claims, 15 Drawing Sheets

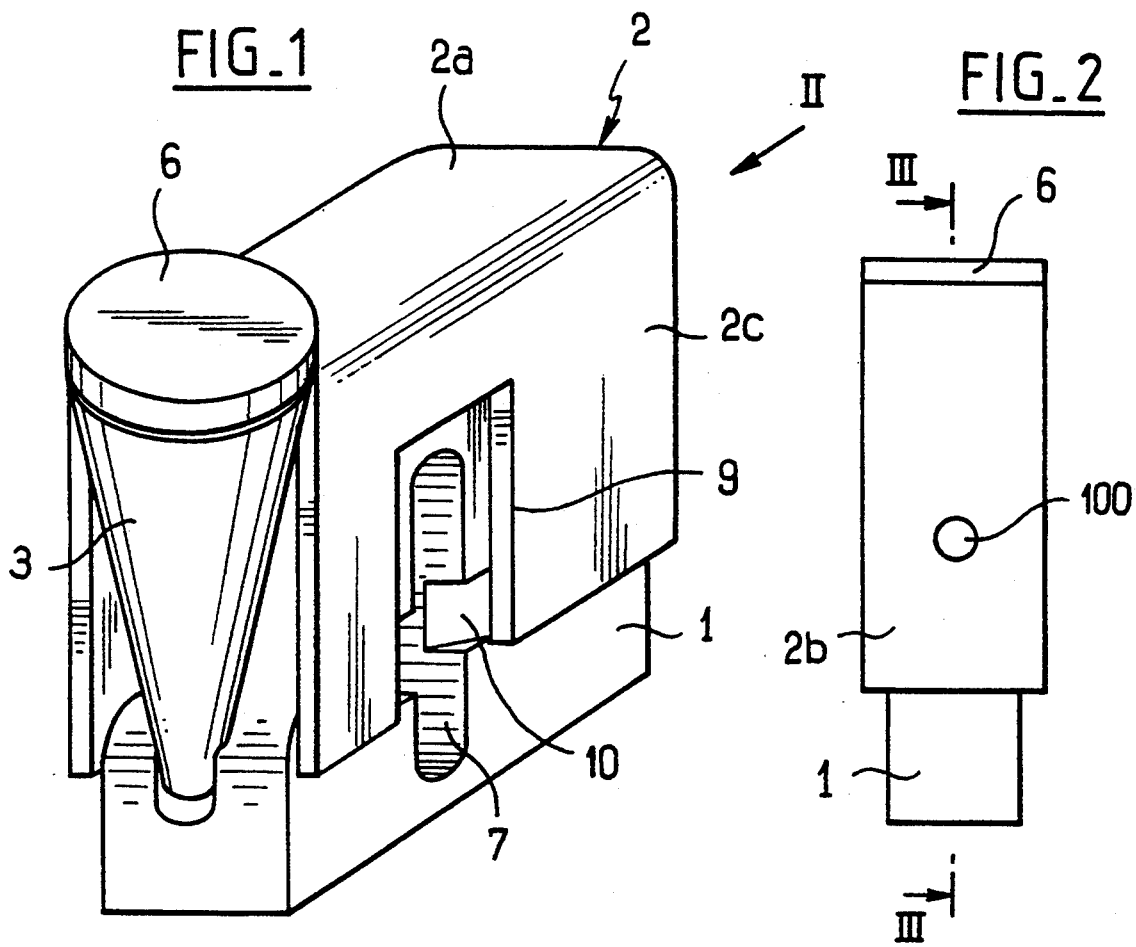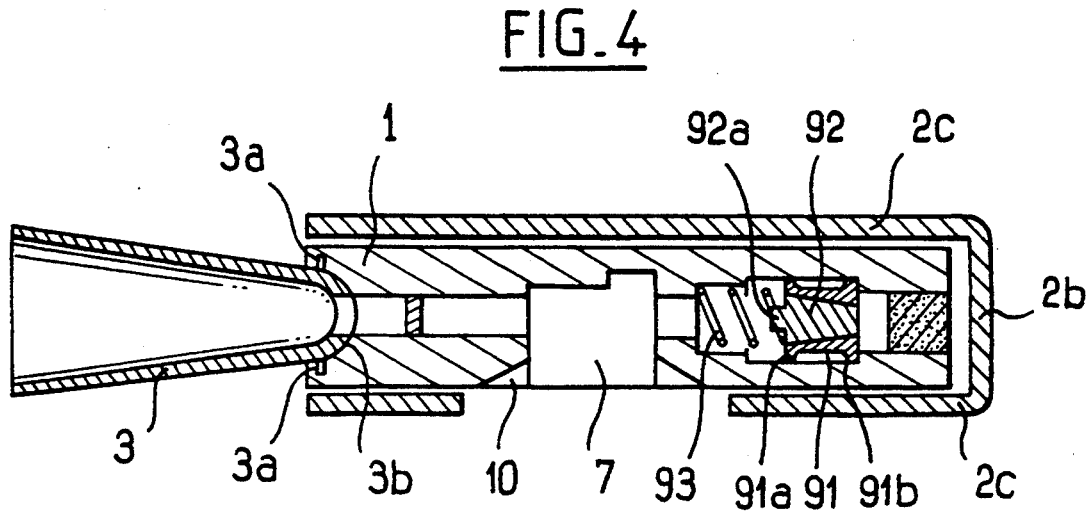

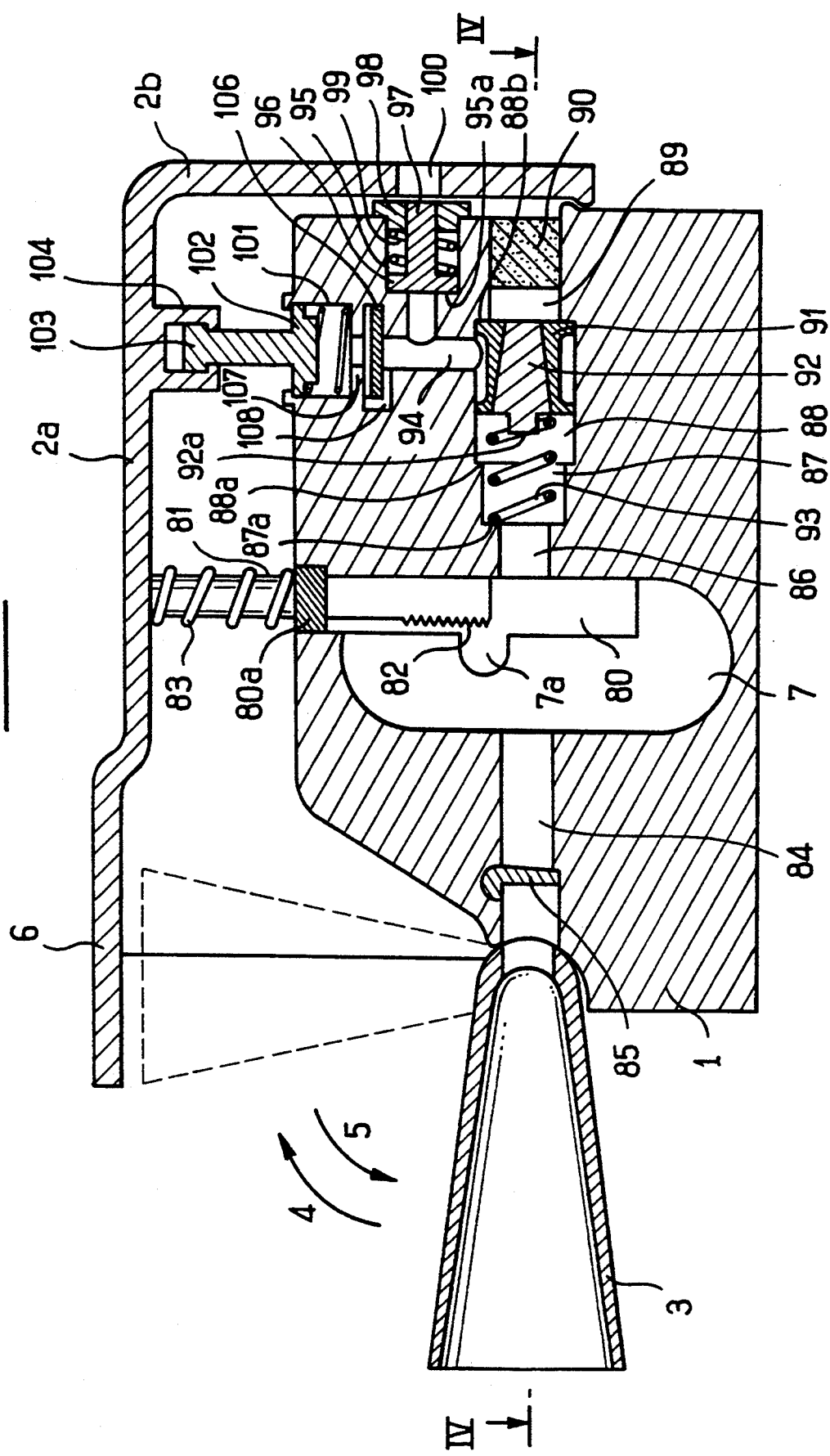

FIG_6a
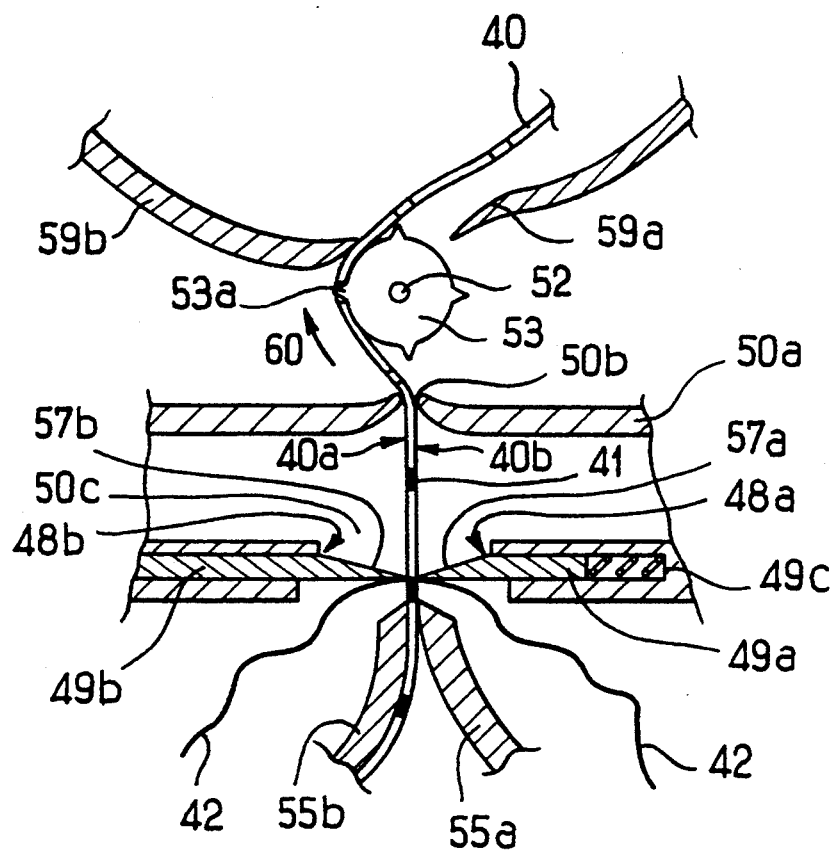
FIG_6b
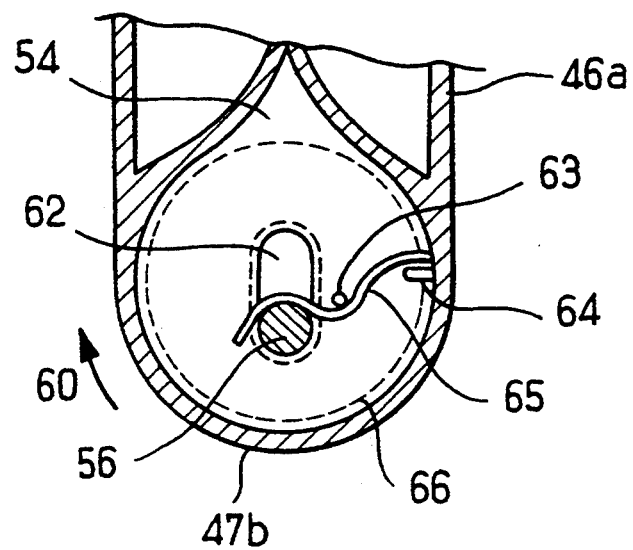

FIG_6c
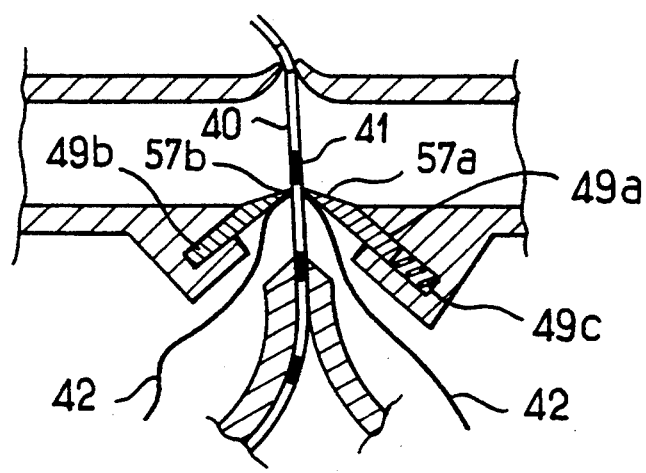
FIG_6d
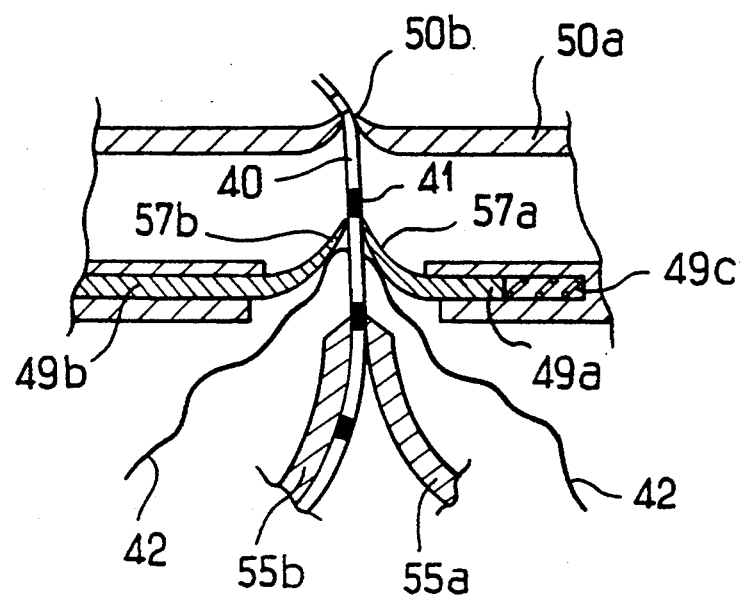

FIG._7
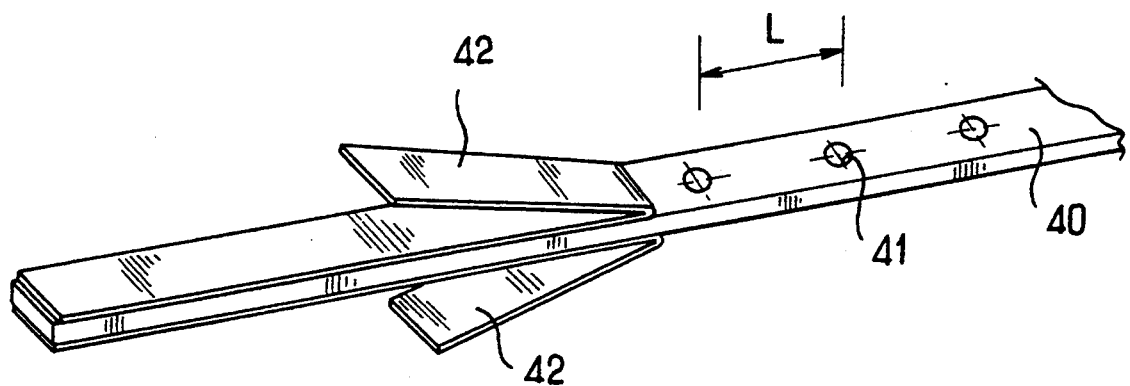
FIG._8
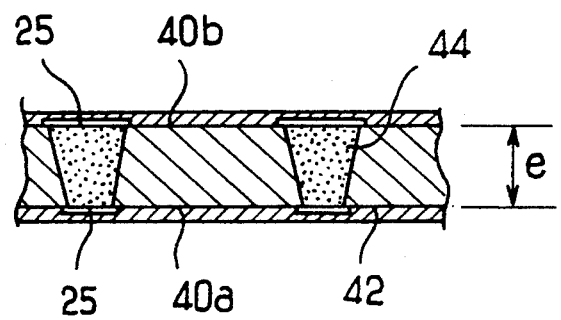

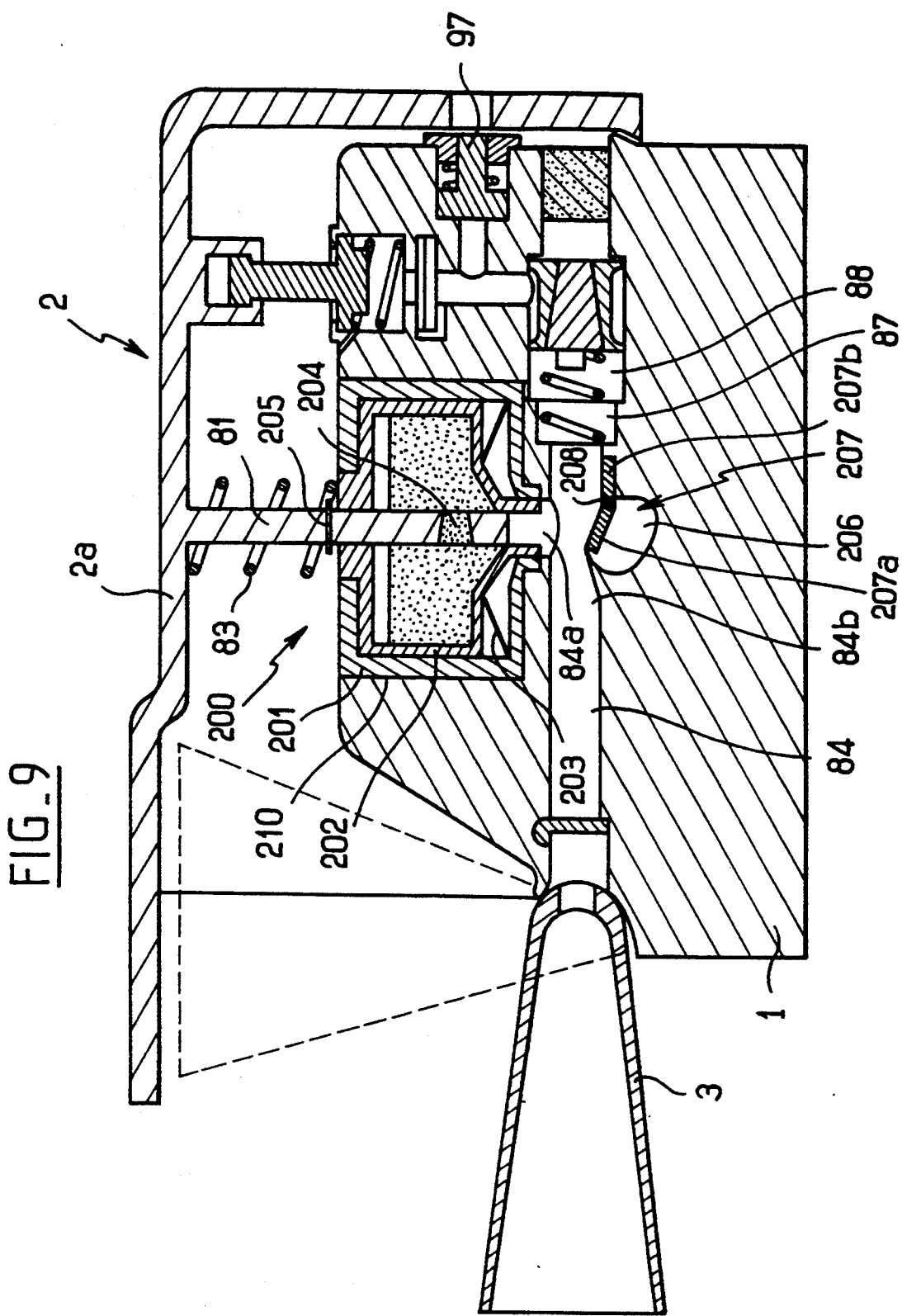
FIG_9

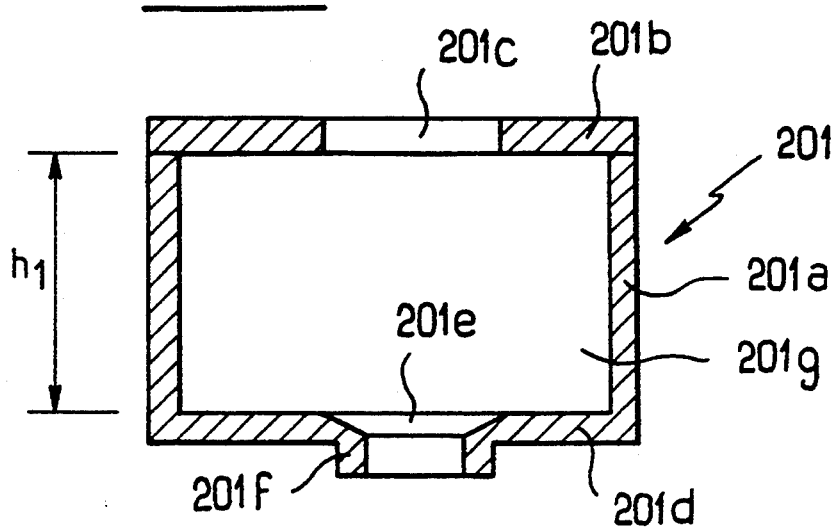
FIG_9a
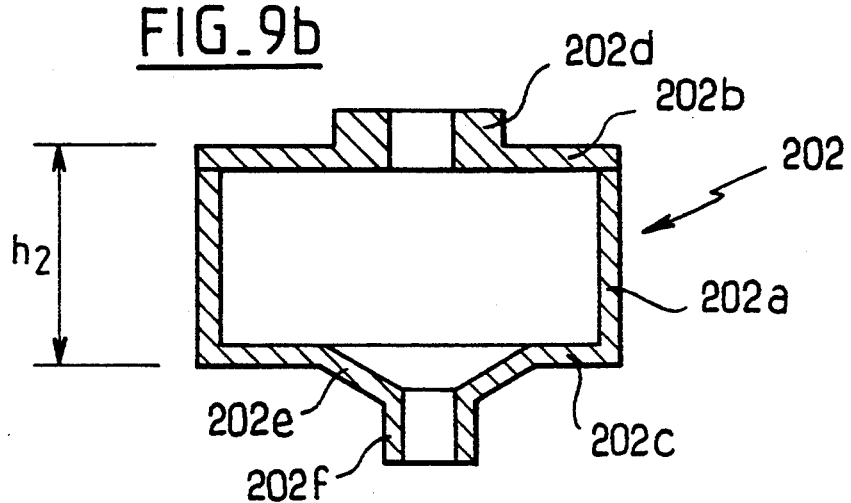
FIG_9b
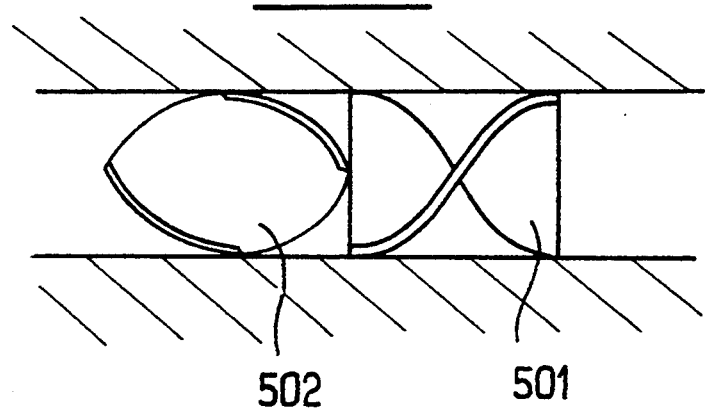
FIG_13

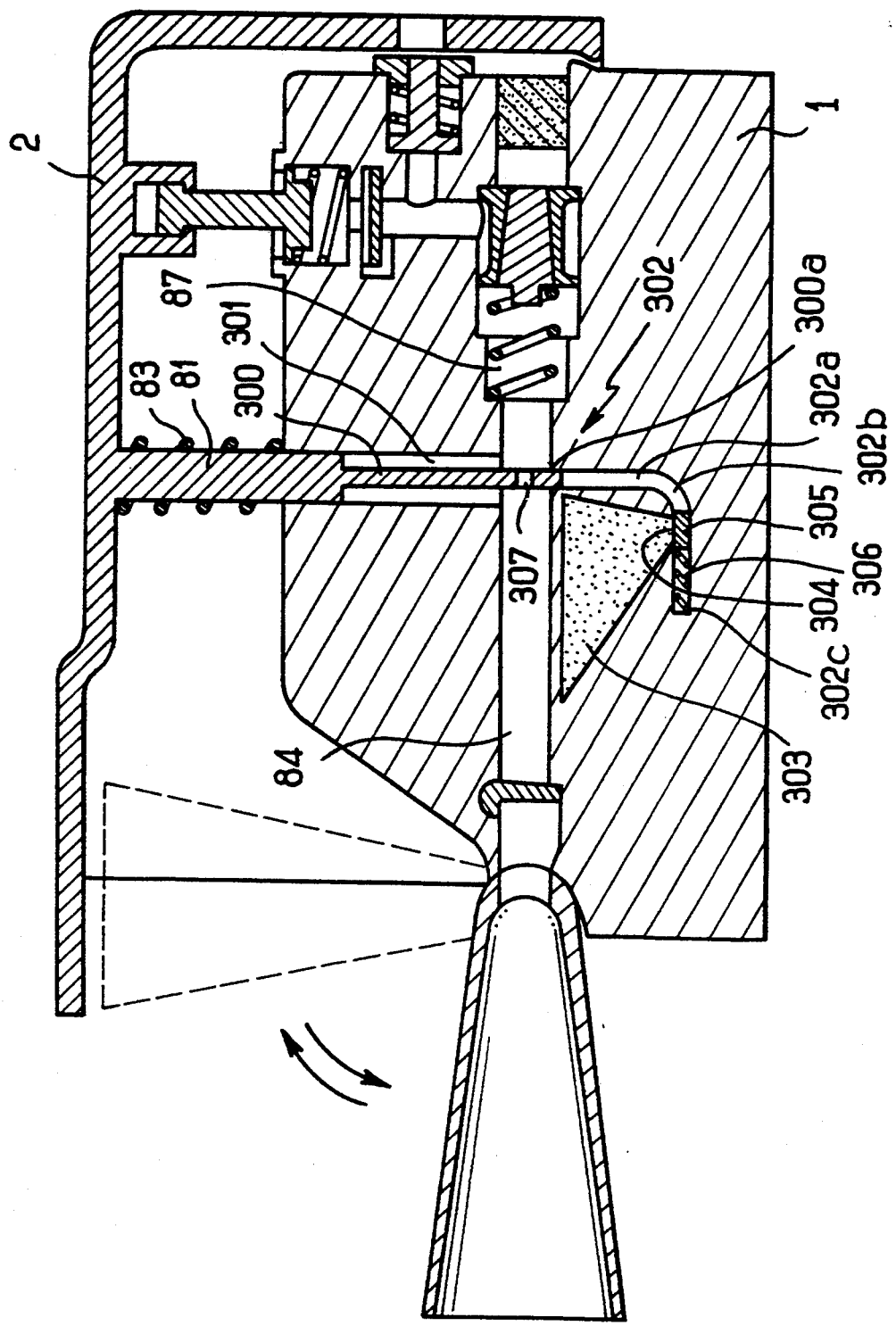
FIG_10

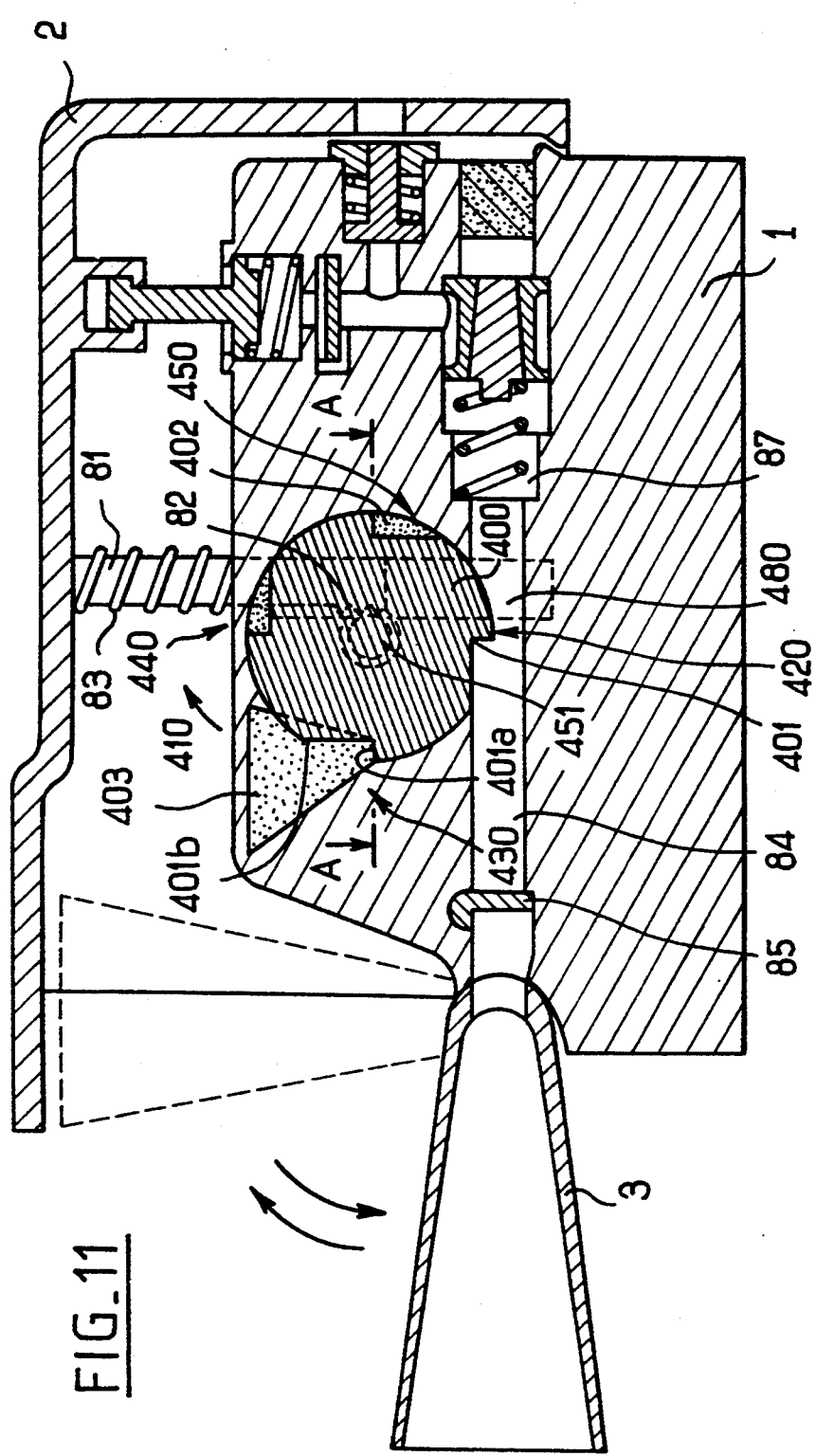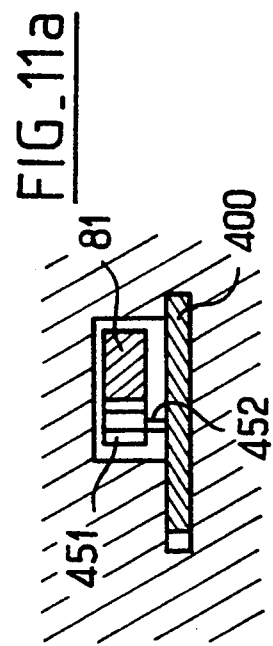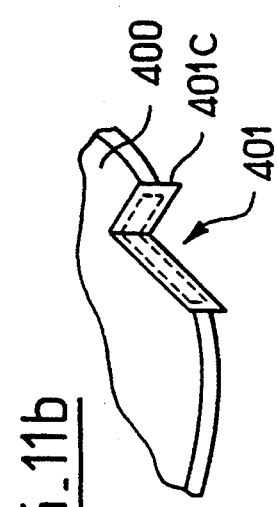

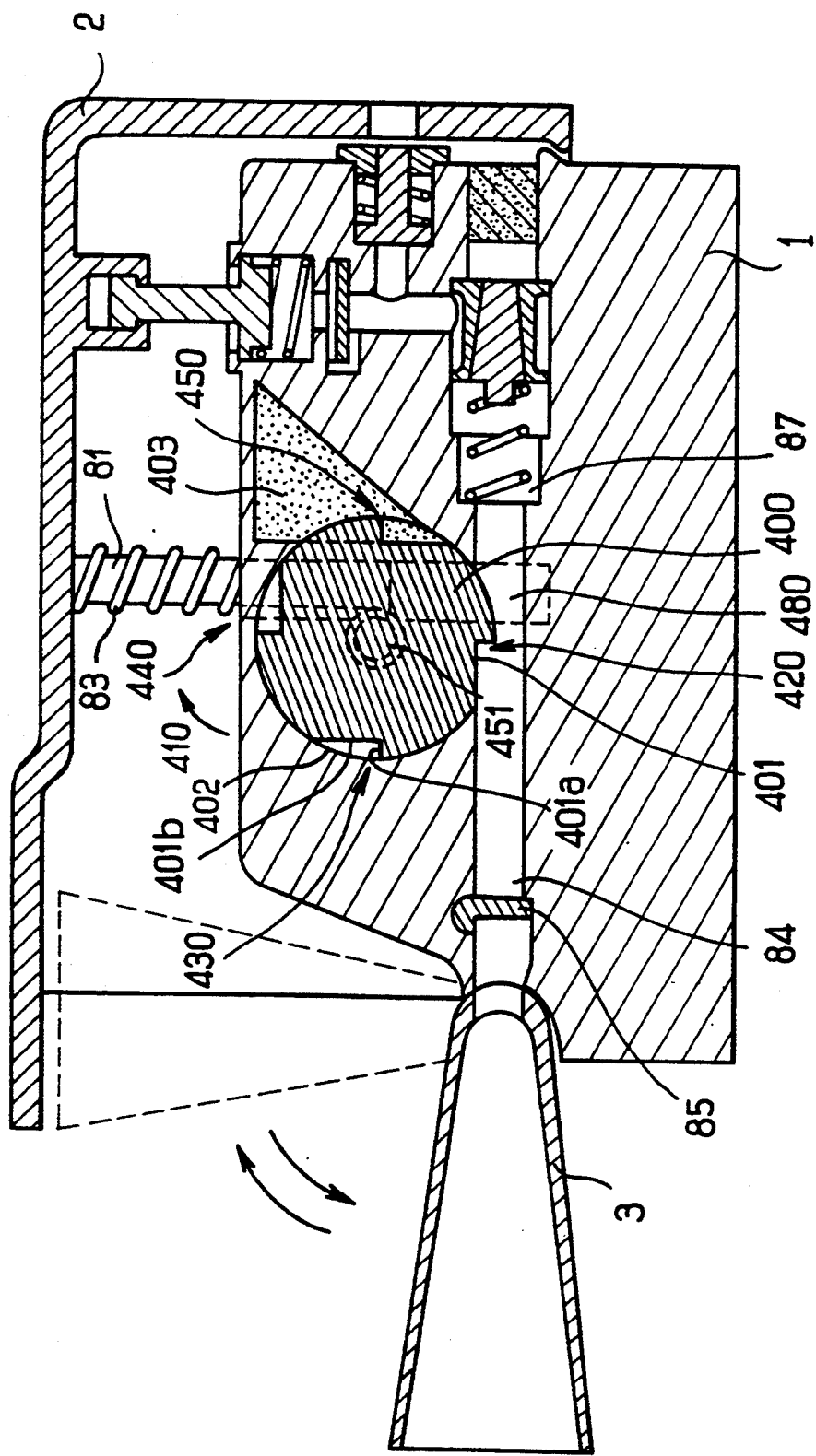
FIG_12

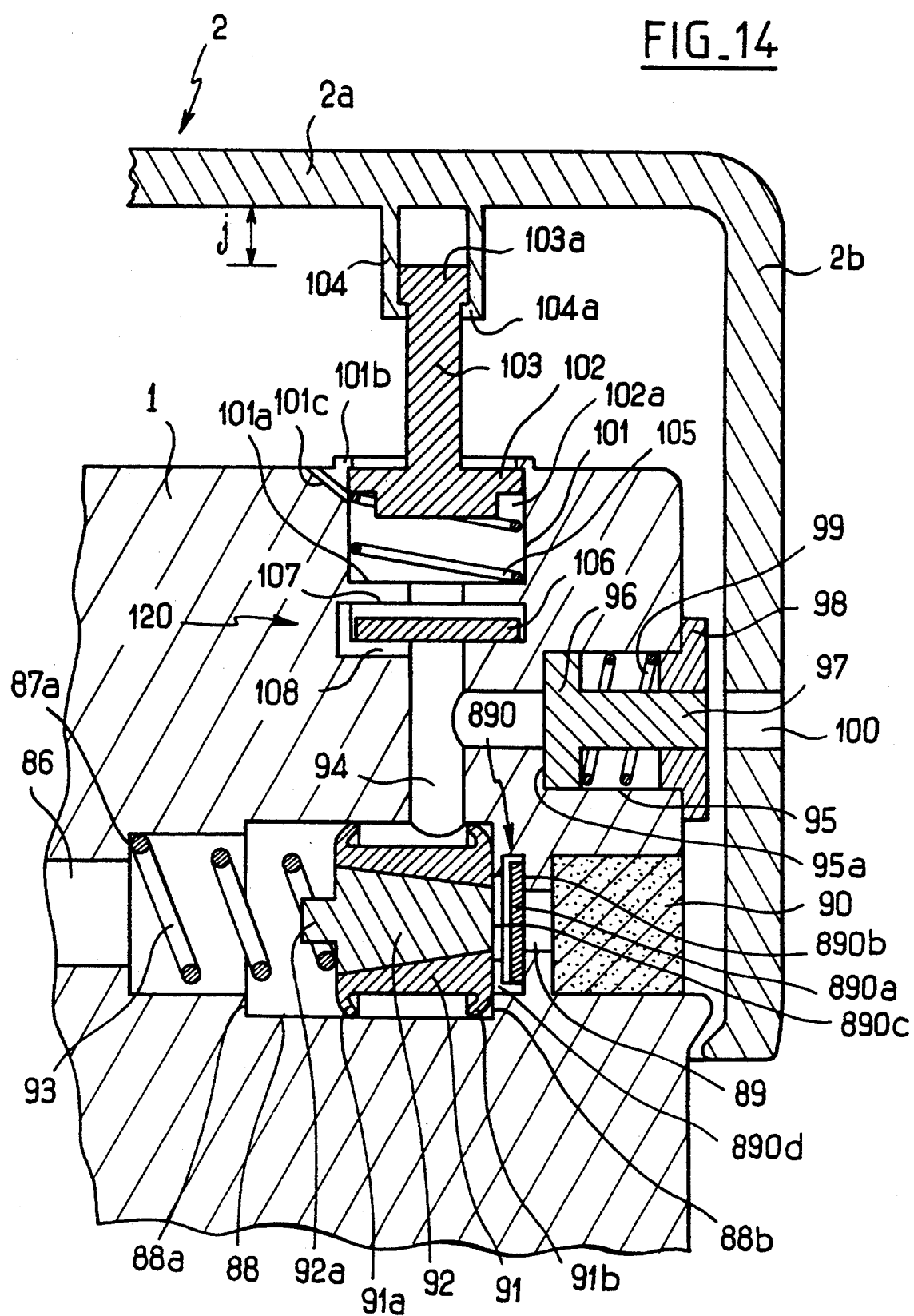

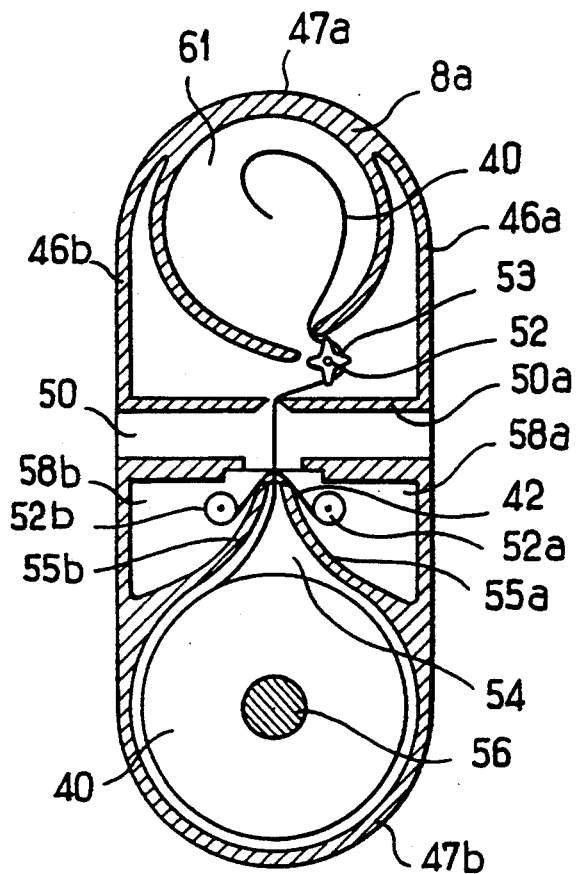
FIG_15
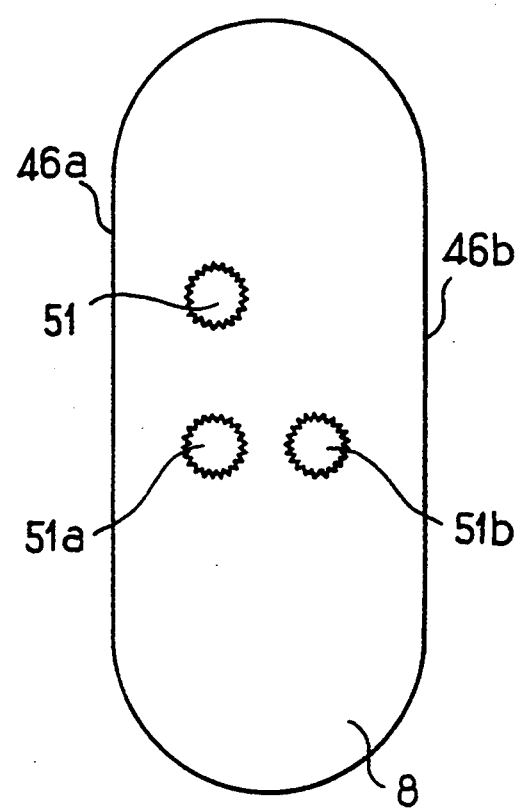
FIG_15a
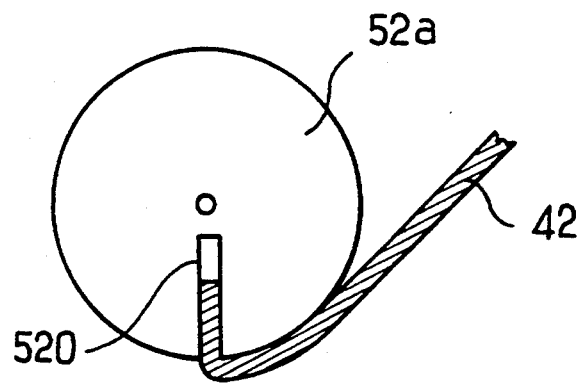
FIG_16

POWDER INHALER WITH SUCTION ACTUATED LOCKING MEANS

BACKGROUND OF THE INVENTION

The present invention relates to a powder inhaler.

One of the present lines of development in pharmaceutical research is pulmonary administration of medication in the form of a dry powder. The lungs constitute a path for easy interchange between inhaled air and the blood, thereby making it possible for an inhaled substance to pass substantially instantaneously into the blood. The effect of the substance is thus quicker than when the same substance is administered via the digestion or by intramuscular injection. In addition, by comparison with an intravenous injection, which also has very rapid effects, inhalation is much easier to use and gives rise to fewer secondary effects.

Pharmaceuticals already exist in dry powder form, generally mixed with excipients. In contrast, the present invention relates to substances in powder form that are very pure and that are not mixed with excipients, thereby avoiding the secondary effects of excipients. As a result, the quantity of substance to be inhaled is very small, generally of the order of 0.2 mg to 5 mg. Furthermore, such substances must be inhaled in doses that are very accurate: ideally, inhaled dose error should be less than 5% by mass.

Devices enabling medication to be inhaled in powder form already exist in the state of the art: however, the accuracy of the dose inhaled using such devices is of the order of 5 mg: such devices are not suitable. Document FR-A-2 334 424 discloses a propellent gas inhaler that is heavy since it is made at least in part of metal, and its operating life is limited by the supply of propellent gas. The placing of a dose of substance to be inhaled is not very practical, and its mechanism is fragile and delicate.

SUMMARY OF THE INVENTION

An object of the present invention is thus to provide an inhaler enabling good accuracy to be obtained on the inhaled dose, and if possible accuracy of better than 5%; Such an inhaler must also satisfy the following conditions:

it must be cheap;
it must be simple and easy to use;
it must be suitable for being transported in the pocket;
it must optionally be capable of dispensing a large number of doses (up to 200, for example);
it must be usable with minimal user suction (e.g. suction at a rate of 20 to 30 liters of air per minute);
it must protect the powder substance against dampness;
it must make wrong operation impossible, e.g. it must prevent the user inhaling a plurality of doses at once; and
it must enable daily consumption to be monitored so that the user is warned before all of the substance to be inhaled has been used up.

The present invention thus provides a powder inhaler comprising a box in which a suction channel is formed enabling a user to inhale a powder, the inhaler being characterized in that it includes a pusher, actuating said pusher enabling a dose of powder to be brought into a position for being sucked into the suction channel, and the box includes a locking mechanism enabling the pusher to be locked after it has been actuated and to be unlocked while the user is sucking in the dose of powder via channel, thereby enabling the actuating means to be actuated again before the next inhalation. The locking mechanism may include locking means responsive to user suction in the suction channel to release said locking mechanism when a pressure reduction is established in the suction channel.

Advantageously, the locking mechanism is pneumatic, means being provided for creating pneumatic pressure by actuating the pusher, the locking mechanism including a latch that is actuatable by said pressure.

The locking mechanism may be constituted by:

- a first piston actuated by the pusher, said piston sliding in a first cylindrical chamber containing air, in such a manner as to compress the air when the pusher is moved towards the box after the pusher has travelled through a certain stroke, said first cylindrical chamber communicating with the outside via an air vent channel when the first piston is in a rest position;

a secondary channel communicating with said first cylindrical chamber via a first non-return valve enabling the air contained in said first cylindrical chamber to pass into said secondary channel, but not the other way;

a second cylindrical chamber opening out into the vicinity of a side wall of the pusher and communicating with said secondary channel;

a second piston sliding in said second cylindrical chamber, said second piston being extended towards said side wall of the pusher by a rod;

spring means disposed in said second cylindrical chamber urging said second piston towards said secondary channel;

a housing in said side wall of the pusher, adapted to receive the rod of said second piston when the pusher is in a rest position after actuation of said pusher has compressed the air contained in the secondary channel by the action of the first piston and of the first non-return valve, thereby having the effect of pushing said second piston and its rod towards said side wall of the pusher;

a third cylindrical chamber extending said suction channel, said third cylindrical chamber being disposed between said suction channel and an air inlet channel opening to the outside of the box, said third cylindrical chamber communicating with the secondary channel;

a fourth cylindrical chamber extending said third cylindrical chamber towards the suction channel, being of diameter smaller than the diameter of said third cylindrical chamber, and being separated from said third cylindrical chamber by a shoulder;

a hollow piston sliding in said third cylindrical chamber; and a second non-return valve of a size suitable for entering into said fourth cylindrical chamber, being disposed between said suction channel and said hollow piston, said second valve being biased by spring means to close said third cylindrical chamber and to push said hollow piston into a position where it interrupts communication between said secondary channel and said third cylindrical chamber, the fourth of said spring means being small enough for suction established by a user in the suction channel initially to displace said hollow piston and said second valve against the bias of the spring, and secondly to disconnect said second valve from said hollow piston, entraining said second valve into said fourth cylindrical chamber, while the hollow piston remains in abutment against said shoulder separating said third cylindrical chamber from said fourth cylindrical chamber. In a first particular embodiment, the first piston is connected with lost motion to the pusher having clearance equal to said stroke after which said pusher actuates said first piston in such a manner that the pusher returns said first piston into its rest position when said pusher itself returns to its rest position. In addition, the first piston may be urged towards the pusher by spring means and said first cylindrical chamber includes abutment means preventing said first piston from leaving said first cylindrical chamber under the effect of said spring means.

Advantageously, a third non-return valve is disposed between the third cylindrical chamber and the air inlet channel, said third valve being adapted to close when higher pressure is created in said third cylindrical chamber and to open when the higher pressure in said third cylindrical chamber ceases.

Advantageously, said suction channel includes a suction valve enabling the user to suck air via the suction channel, but preventing the user from blowing air into said suction channel.

The suction channel may also outwardly extend by a tubular mouthpiece.

The mouthpiece may be rotatably mounted so as to be capable, selectively, of being placed in an in-use first position in which it communicates with said suction channel, or in a storage second position in which said mouthpiece engages beneath a portion of the pusher in such a manner as to lock it.

Said suction channel may include powder break-up means. Said powder break up means may include at least two screw portions that are angularly offset about a common longitudinal axis so as to establish discontinuity in the flow of air sucked in by the user.

In one embodiment of the inhaler of the invention, the box may include a housing for receiving a removable cassette containing doses of powder to be inhaled, said cassette itself including a channel extending the suction channel when the cassette is inserted in the housing of the box.

In which case, said cassette may contain a flexible strip carrying said doses of powder to be inhaled, and said cassette includes strip drive means which, when the cassette is installed in the box are mechanically engaged with drive means driven by the pusher so as to expose in the channel of the cassette, a portion of the strip carrying a new dose of said powder, each time the pusher is actuated. Advantageously, said strip has two faces and holes opening out into both faces and distributed along the length of said strip, each of said holes being filled with a dose of powder to be inhaled, each of the two faces of the strip including an adhesive protective film closing said holes, said strip drive means being disposed on one side of the cassette channel and driving the strip by traction, the strip passing through the cassette channel while occupying a plane that is substantially perpendicular to said channel, the cassette including delamination means disposed relative to the cassette channel opposite to the strip drive means, said delamination means being adapted to remove said protective films from the strip before the strip penetrates into the channel of the cassette. Said adhesive films may include adhesive-free zones facing the holes in the strip. The holes in the strip may be frustoconical, flaring towards said suction channel.

Advantageously, said actuator means driven by the pusher comprise a rod secured to the pusher and provided with at least one rack, said strip drive means including a drive wheel rotated by a gear wheel that meshes with the rack, said drive wheel being connected to the gear wheel by a free-wheel mechanism enabling the gear wheel to drive said drive wheel when said gear wheel rotates in a preferred direction of rotation, but not driving the drive wheel when said gear wheel rotates in the opposite direction. In which case, the means for delaminating the cassette strip may include two spools onto which the two films of the strip are wound respectively, each of the protective film wind-up spools being rotated by a respective gear wheel that meshes with at least one rack of the rod secured to the pusher, and the protective film wind-up spools are connected to their respective gear wheels via a free-wheel mechanism enabling each gear wheel to drive the corresponding wind-up spool when said gear wheel rotates in a preferred direction of rotation, but not driving the wind-up spool when the gear wheel rotates in the opposite direction. In any event, said delamination means may include two blades each applied against-one of the faces of the strip.

In a particular embodiment of the inhaler of the invention, the box includes a tank containing powder to be inhaled, the pusher including a rod pierced by a hole parallel to the suction channel and sliding between a raised first position in which the hole slides inside the tank, and a lowered second position in which the hole through the rod lies in said suction channel, and the box further includes means for ejecting the dose of powder to cause the dose of powder contained in the hole of the rod to be ejected therefrom when said rod is in its lowered position. The ejection means may be a flap mounted to pivot about an axis, said flap comprising two portions on either side of the axis, a first portion being capable of pivoting into a recess communicating with said suction channel when the rod of the pusher reaches its lowered position, while the second portion of the flap strikes an end of the hole of the rod, thereby projecting the dose of powder contained in said hole out from said hole into the suction channel. Said first portion of said flap may isolate said recess that communicates with said suction channel when said pusher is in its raised position.

Advantageously, the tank of powder comprises an inner tank containing the powder and through which the rod of the pusher slides, said inner tank sliding with lost motion inside an enclosure secured to the box, said inner tank being urged towards the pusher by resilient means, and the rod includes external relief suitable for driving the inner tank against the bias of the resilient means when the rod is pushed into the box, and then to retract to enable the rod to slide through the inner tank once the bias of the resilient means reaches a limit value or once said inner tank reaches an abutment position.

The tank may include the powder includes at least one upwardly flared bottom portion.

In a particular embodiment of the inhaler of the invention, the pusher includes a rod sliding inside a well of the box between a raised first position and a lowered second position, said well communicating with the suction channel, the rod being extended by a flexible tongue pierced by a hole having an inside volume equal to the volume of one dose of powder, said hole being parallel to the suction channel and lying in said suction channel when the pusher is in its raised position, the box including a guide channel for the flexible tongue communicating with said suction channel, including a vertical portion in line with said flexible tongue, a curved portion, and then a horizontal portion situated beneath a tank of powder and communicating with said tank via an opening, said opening being capable of being closed by a slider sliding in said bottom portion of said guide channel, said slider being biased by a spring towards a position in which it closes the opening of the tank, the flexible tongue being adapted to push the slider against the bias of the spring so as to bring the hole of said tongue beneath the opening of the tank when the pusher is in its lowered position. A bottom portion of the tongue may remain in said guide channel when the rod is in its raised position.

Advantageously, said tank includes at least a bottom portion that is upwardly flared.

In a final embodiment of the inhaler of the invention, the pusher includes a rod sliding in a well of the box and provided with a rack, the box including a wheel rotatably mounted in a substantially circular housing, said rod including regularly spaced apart peripheral notches each of inside volume equal to the volume of a dose to be inhaled, said wheel being provided with a shaft linked to a gear wheel by a free-wheel mechanism such that when the gear wheel rotates in a preferred direction of rotation it drives the wheel, but when it rotates in the opposite direction, the wheel is not driven, the gear wheel meshing with the rack of the rod of the pusher, the box including a tank into which the wheel penetrates so as to fill the notches with powder, the wheel penetrating into the suction channel, and the notches being disposed in such a manner that a new notch penetrates into the suction channel each time the pusher is actuated, thereby bringing a new dose of powder into said suction channel.

Advantageously, each of said notches includes a radial face having a normal that is directed in the preferred direction of rotation, and a face perpendicular to said radial face. Said tank may include at least an upwardly flared bottom portion. Said notches may be provided with peripheral sealing lips which bear resiliently against said substantially circular housing when said notches are within said housing.

BRIEF DESCRIPTION OF THE DRAWINGS

Other characteristics and advantages of the invention appear on reading the following detailed description of various embodiments of the invention, given by way of non-limiting example and described with reference to the accompanying drawings.

In the drawings:

FIG. 1 is a diagrammatic perspective view of a first embodiment of an inhaler according to the present invention;

FIG. 2 is a view of the FIG. 1 inhaler seen along direction II;

FIG. 3 is a section on line III—III of the inhaler shown in FIGS. 1 and 2;

FIG. 4 is a section view on line IV—IV of the inhaler of FIGS. 1 to 3;

FIG. 5b is a section view on line B—B through the drive gear wheel of FIG. 5a;

FIG. 6a is a detail view of FIG. 6, showing how the strip is driven and delaminated;

FIG. 6b is a detail view of FIG. 6 showing one example of a tensioning wheel;

FIG. 6c is a detail view of a variant of the cassette delaminating blades;

FIG. 6d is a detail view of another variant of the cassette delaminating blades;

FIG. 7 is a fragmentary view of the strip contained in the cassette of FIG. 5;

FIG. 8 is a longitudinal section view of the FIG. 7 strip;

FIG. 9 is a section view through a second embodiment of the inhaler in accordance with the invention, and including a powder tank;

FIG. 9a is a section view through the enclosure of the powder tank of the FIG. 9 inhaler;

FIG. 9b is a section view of the internal powder tank of the FIG. 9 inhaler;

FIG. 10 is a section view through a third embodiment of an inhaler in accordance with the invention;

FIG. 11 is a section view through a fourth embodiment of an inhaler in accordance with the invention;

FIG. 11a is a fragmentary section view on line A—A of FIG. 11;

FIG. 11b is a detail view of the wheel of the FIG. 11 inhaler;

FIG. 12 is a section view through a variant of the FIG. 11 inhaler;

FIG. 13 is a detail view showing screw portions that may be installed in the suction channel of all of the embodiments of the inhaler of the invention;

FIG. 14 is a view similar to FIG. 3a, showing a variant inhaler in accordance with the invention;

FIG. 15 is a view similar to FIG. 6, for a variant cassette;

FIG. 15a is a front view of the FIG. 15 cassette;

FIG. 16 is a detail view of FIG. 15; and

DETAILED DESCRIPTION OF THE PREFERRED EMBODIMENTS

Figure 3A:
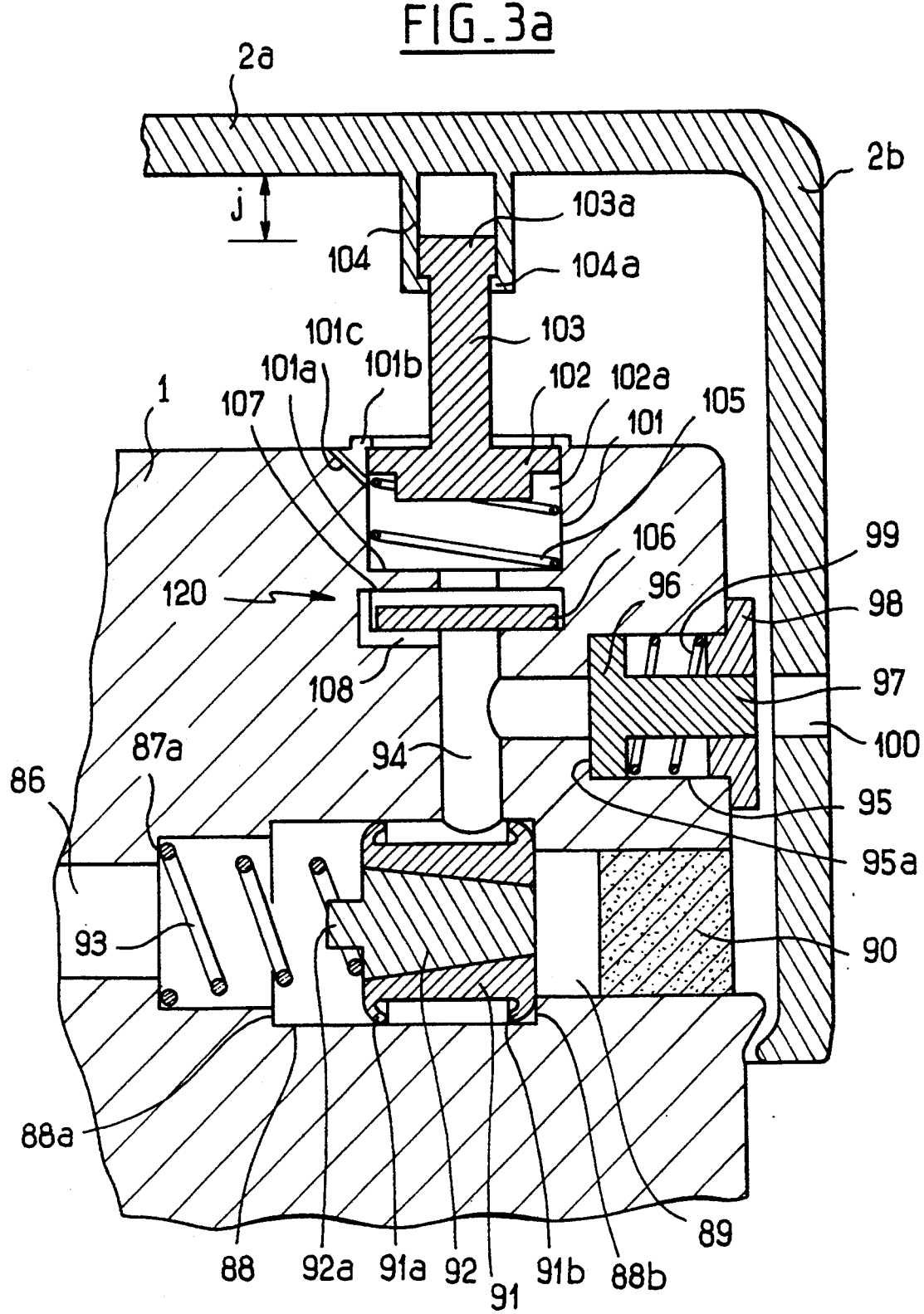
FIG. 3a is a detail view of FIG. 3.

In the following detailed description, the same references designate portions that are identical or "similar. In order to clarify the description, terms such as "up", "down", "vertical", "horizontal", etc. are sometimes used: these terms are not limiting and serve merely to facilitate understanding of the drawings.

FIG. 1 shows a first embodiment of an inhaler in accordance with the invention, which may generally be made of molded plastic and which comprises a fixed box 1 covered by a pusher 2 that is vertically movable relative to the box 1.

In the particular embodiment shown in FIGS. 1 to 4, the pusher 2 comprises a horizontal top wall 2a that is generally rectangular in shape, and that is extended downwards along three sides, respectively by a vertical rear wall 2b and by two vertical side walls 2c. At its end that is not extended downwards by a vertical wall, i.e. at its front end, the horizontal top wall 2a is extended horizontally by a projection 6 secured to said horizontal wall 2a, and in this case in the form of a disk.

The box 1 includes a retractable mouthpiece 3 which is mounted to rotate in a vertical plane in the directions represented by arrows 4 and 5 in FIG. 3.

As shown in FIG. 3, the mouthpiece 3 is constituted in this case by a tubular member that is somewhat flared, but it could have any other shape. As shown in FIG. 4, the mouthpiece 3 may include stub axles 3a rotatably received in bearing-forming housings in the box 1. However, the mouthpiece 3 may also be rotatably mounted on the box 1 by any other known means, e.g. by a ball and socket type joint. In any event, a rear portion 3b of the mouthpiece 3 is in sealed contact with the box 1.

The mouthpiece 3 can thus be placed in a horizontal position when a user desires to inhale a dose of medication, as explained below, or else it may be put in a vertical, rest position, as shown in FIG. 1.

When the mouthpiece 3 is in this vertical position, the projection 6 on the pusher 2 prevents said pusher 2 moving downwards, i.e. towards the box 1, thereby preventing the pusher being actuated by mistake.

Figure 6:
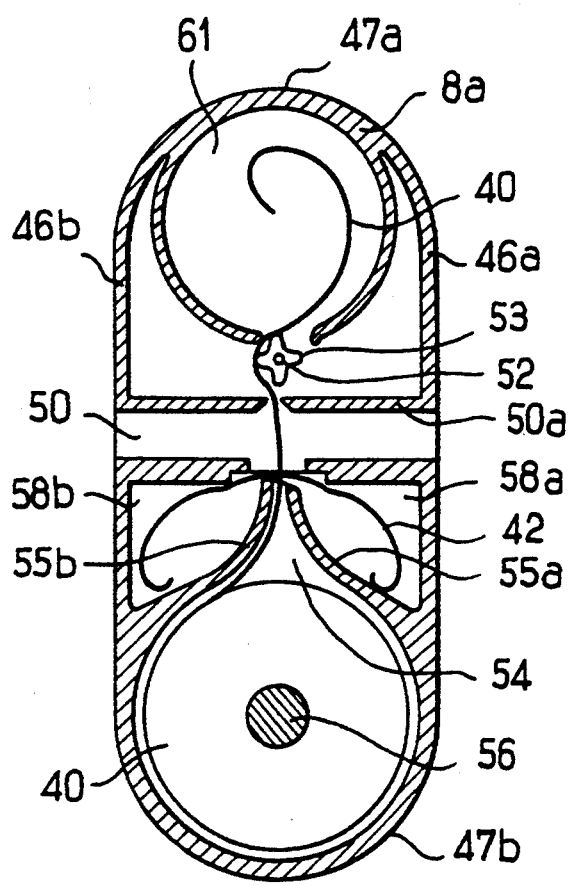
FIG. 6 is a section view on line VI—VI of the FIG. 5 cassette.
Figure 5:
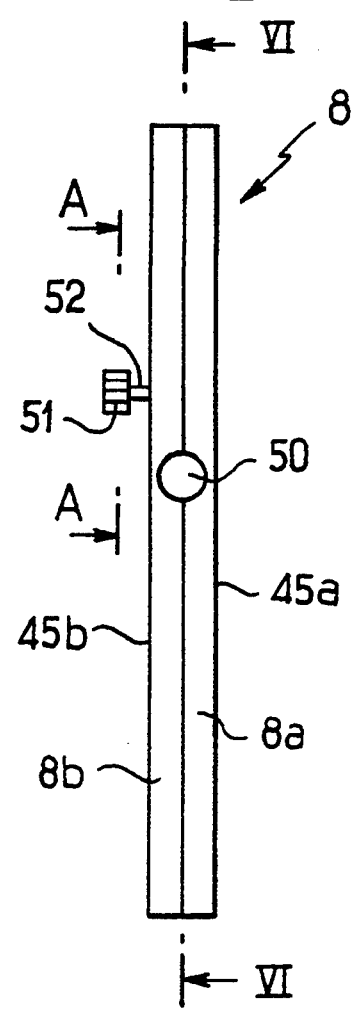
FIG. 5 is a side view of a refill cassette for the inhaler of FIGS. 1 to 4.

The box 1 further includes a housing 7 suitable for receiving a cassette 8 containing doses of powder, as shown in FIGS. 5 and 6. The cassette 8 may contain a large number of doses of powder, for example as many as 200. The said cassette 8 is removably secured in the housing 7 by any known means, e.g. by snap-fastening. Thus, when said cassette 8 is empty, i.e. when all of its doses of powder have been inhaled, it may be removed from the housing 7 by the user and replaced with a new cassette.

To do this, the housing is made accessible via a notch 9 in the pusher 2, and the box 1 includes two recesses 10 on either side of the housing 7, enabling the user to grasp a cassette 8 between two fingers in order to extract it from said housing 7.

By way of example, the cassette 8 may be about 75 mm high, about 30 mm wide, and about 8 mm thick. It contains a flexible strip 40 for storing microdoses of the substance to be inhaled, and shown in FIGS. 7 and 8. The strip 40 has two faces 40a and 40b separated by a thickness e.

The storage strip 40 includes holes 41 opening out on both faces thereof and distributed along said strip at a constant pitch L in this particular example, but the pitch could optionally be variable along the strip 40. The holes 41 are filled with powder 44 to be inhaled, each hole 41 having an inside volume equal to the volume of one dose to be inhaled. The volume of the dose is determined by the size of the holes 41 and by the thickness e of the strip. For example, with a powder of known density, such as LOMUDAL ®, a 0.5 mg dose corresponds to a volume of 1.91 $mm^3$, which, by way of example, corresponds to a strip having a thickness $e=0.25$ mm and a hole 41 having a diameter of 3.2 mm, assuming that the holes 41 are cylindrical. With a powder of the same density, a 5 mg dose would correspond, for example, to $e=0.5$ mm and to holes 41 having a diameter of 7 mm, if the holes are cylindrical. Clearly, with other powders of different density, and for doses of different sizes, these dimensions may be altered.

The width of the strip may be 5 mm to 10 mm, for example, depending on the volume of each microdose, and the length of the strip may be much as one meter or more, depending on the number of doses and the pitch L of the holes 41. Naturally the size of the cassette 8 depends on the length, on the width, and on the thickness of the strip 40.

An adhesive protective film 42 is applied to each face of the strip 40, which film is easily delaminated from the strip by pressing a blade with a certain amount of pressure against each of the faces of said strip and by pulling the strip 40 between said blades, with or without the blades exerting a cutting effect where the strip 40 joins the films 42. Thus, inside the cassette 8, whenever the inhaler is actuated so as to prepare an inhalation, in the manner explained below, the protective films on the faces 40a and 40b of the strip 40 of doses are delaminated therefrom so as to reveal a hole 41 filled with one dose of powder.

When suction is established on one of the faces of the strip, e.g. the face 40b, because of a sucking action by the user, the microdose of powder contained in the hole 41 is sucked out from the hole 41 into the lungs of the user. As shown in FIG. 8, the holes 41 may be frusto-conical: the holes 41 are then larger on the face 40b than on the face 40a, i.e. they flare in the direction of suction, thereby facilitating and enhancing the expulsion of the powder when suction occurs on said face 40b of the strip 40. However, the holes 41 could equally well be cylindrical, without going beyond the ambit of the present invention.

Advantageously, the protective films 42 do not include adhesive in their zones 25 overlying the holes 41, so as to avoid the films entraining any fraction of the doses of powder contained in the holes 41 when they are removed by delamination.

A particular example of the cassette 8 containing the strip 40 of microdoses is shown in FIG. 5. It comprises two half-shells 8a and 8b which may be made of plastic, and which may be assembled together by snapfastening, by adhesive, by ultrasonic welding, or by any other means. The cassette 8 is generally planar in shape and thin. In the embodiment shown in FIGS. 5 and 6, it has two parallel plane faces 45a and 45b delimited by two parallel rectilinear sides 46a and 46b and by two opposite semi-circular sides 47a and 47b.

The cassette 8 includes an internal channel 50 passing through it parallel to its two faces 45a and 45b and perpendicular to its rectilinear sides 46a and 46b, said internal channel 50 opening out in both of the rectilinear sides 46a and 46b. The channel 50 is shown as being circular in section, but it could have any other section. Said channel 50 is delimited by a cylindrical wall 50a longitudinally separated into two halves each molded in a respective one of the two half-shells 8a and 8b. As shown more clearly in FIG. 6a, the wall 50a of the channel 50 includes a slot 50b substantially perpendicular to the faces 45a and 45b of the cassette, and situated substantially halfway between the sides 46a and 46b of said cassette. The slot 50b may occupy substantially the entire thickness of the channel 50 between the faces 45a and 45b of the cassette, and its width (i.e. its smallest dimension) may be substantially equal to the thickness e of the strip 40.

The wall 50a of the channel 50 further includes a recess 50c also disposed halfway between the sides 46a and 46b of the cassette, and opposite to the slot 50b. Like the slot 50b, the recess 50c may extend over substantially the entire thickness of the channel 50 between the faces 45a and 45b of the casette.

Running from the edges of the recess 50c, two slots 48a and 48b formed in the wall 50a extend respectively towards the sides 46a and 46b of the cassette, and substantially over the entire thickness of the channel 50 between the faces 45a and 45b, being perpendicular to said faces 45a and 45b. Two blades for delaminating the strip 40 are inserted in said slots 48a and 48b, the blades may be metal blades and they are given respective references 49a and 49b. Each of the blades 49a and 49b has an end in contact with the strip 40, respectively referenced 57a and 57b, and the strip 40 is pulled between them prior to penetrating into the channel 50, as described below.

Advantageously, one of the blades, e.g. the blade 49b, may be a force-fit in its slot 48b so as to be held fast therein, while the other blade 49a is slidably mounted in its slot 48a and is urged towards said fixed blade 49b by resilient means such as a spring 49c mounted in the slot 48a. Thus, when the strip 40 is pulled between the ends 57a and 57b of the blades, said ends 57a and 57b are always in resilient contact with the strip 40 whatever surface defects may be presented by said strip 40. In particular, when the strip 40 has a bulge, this resilient mounting prevents the blades 49a and 49b cutting through said strip 40.

Said ends 57a and 57b may be sharpened or otherwise, depending on whether it is desired that they should exert a cutting effect at the joint between the strip 40 and its films 42 in order to delaminate said films 42. Said ends 57a and 57b are adjacent to each other and they delimit a slot parallel to the slot 50b and of width substantially equal to the width e of the strip 40 of microdoses.

If they are sharpened, each of said ends 57a and 57b may include a plane first face in line with the respective blade 49a or 49b, and a second face that is at an angle relative thereto. Advantageously, the non-chamfered plane face is disposed to face the direction in which the strip 40 arrives prior to passing between said ends 57a and 57b.

As shown in FIG. 6, the cassette 8 includes a storage housing 54 containing the microdose strip 40 wound onto a cylindrical wheel 56. Inside the storage housing 54, said strip 40 includes the adhesive protective films 42 stuck on its two faces 40a and 40b, and its holes 41 are filled with the powder to be inhaled.

The housing 54 is laterally delimited by the semicircular side 47b of the cassette 8, and by two arms 55a and 55b integrally molded with the cassette and extending from respective sides 46a and 46b of the cassette to the vicinity of the sharp ends 57a and 57b of the blades 49a and 49b.

In the vicinity of the blades 49a and 49b, the arms 55a and 55b are spaced apart from each other by a distance substantially equal to the thickness e of the strip 40. The arms 55a and 55b are disposed so as to form a slot parallel to the slot 50b and to the slot delimited by the blades 49a and 49b, and they are disposed so that all three slots are in alignment.

Starting from the storage housing 54, the strip 40 passes between the arms 55a and 55b which guide it, and then between the blades 49a and 49b, after which it passes through the channel 50, perpendicularly to said channel, and into the slot 50b. After passing between the blades 49a and 49b, the strip 40 no longer includes its two protective films 42. When the strip 40 is pulled from the storage housing 54 in the manner described below, said films 42 are removed by being delaminated therefrom as the strip 40 passes between the ends 57a and 57b of the blades 49a and 49b.

On either side of the arms 55a and 55b, the cassette 8 includes two housings 58a and 58b for containing the delaminated films 42. The housing 58a is delimited laterally by the arm 55a, the side 46a of the cassette, and the wall 50a of the channel 50. Similarly, the housing 58b is delimited by the arm 55b, the side 46b, and the wall 50a.

After passing through the channel 50, and into the slot 50b, the strip 40 extends to a drive wheel 53 that is clearly visible in FIG. 6a. The wheel 53 is secured to a rotary shaft 52 that passes through the face 45b of the cassette so as to extend to an eternal drive gear wheel, as shown in FIG. 5. With reference to FIG. 6a, the drive wheel 53 has sprockets 53a uniformly distributed around its periphery. In this particular assembly, there are four such sprockets 53a at 90° intervals from one another. In addition, the cassette 8 includes two arms 59a and 59b extending from respective sides 46a and 46b of the cassette to the vicinity of the wheel 53. The arm 59b is substantially tangential to the wheel 53 and is offset from said wheel 53 by a distance substantially equal to the thickness e of the strip 40. In this case, the arm 59b extends in the direction of rotation of the wheel 53. It may also be urged resiliently towards the wheel.

The strip 40 passes over the wheel 53 whose sprockets 53a engage in the already-used holes 41 in the strip. The strip 40 is also held against the wheel 53 by the arm 59b. Advantageously, the arm 59b is somewhat flexible, so as to press resiliently against the strip 40, urging said strip against the drive wheel 53. Before installing the strip 40 in the cassette 8, said strip 40 has a certain length starting from one end of the strip 40 that does not include the protective films 42, and that has holes 41 that are empty. This makes it possible to install the strip 40 in the cassette 8, by engaging the sprockets 53a of the wheel 53 in said empty holes 41 that are not protected by the films 42. The length of strip 40 that does not have protective films must be sufficient to enable it to extend slightly beyond the delaminating blades 49a and 49b starting from the wheel 53. Thus, when the strip 40 is pulled out from its storage housing by the drive wheel 53, the protective films 42 of the strip 40 come into abutment against the blades 49a and 49b, and they are delaminated.

The diameter of the wheel 53 and the angular spacing of the sprockets 53a of said wheel 53 are adapted so that when the wheel 53 rotates through one-fourth of a turn in a direction of rotation 60, each sprocket 53a engages in succession in an already-used hole 41 of the strip 40, thereby driving said strip.

The arms 59a and 59b of the cassette 8 define a housing 61 for recovering the strip 40 after it has passed over the wheel 53. In a variant, it is possible for the cassette 8 to be designed so that the strip 40 is wound onto the wheel 53 instead of being stored roughly in the recovery housing 61. Under such circumstances, the pitch L of the holes 41 needs to vary along the length of the strip.

In the example shown in the drawings, the constant pitch L between adjacent pairs of holes 41 in the strip 40 is such that whenever the wheel 53 rotates through one-fourth of a turn in the direction 60, a length of strip 40 exactly equal to L is pulled out from the storage housing 54 and is delaminated by the metal blades 49a and 49b so that a hole 41 containing one dose of powder is uncovered and brought into the channel 50, and always occupies the same position therein. This also requires high accuracy in the distance L, in the diameter of the drive wheel 53, and in the positioning of the sprockets 53a on said wheel 53.

Since the strip 40 is perpendicular to the channel 50, the hole 41 situated in said channel 50 is parallel to the direction of the channel. If a user sets up air suction by sucking into the channel 50, on the same side as the face 40b of the strip 40, the user will inhale the dose of powder contained in said hole 41 as explained above with reference to FIG. 8. The strip 40 may occupy the entire width of the channel 50 in the casette, or else it may be narrower than the channel, particularly if the holes 41 are very small, so as to limit the headloss developed in the flow of sucked-in air, so as to put a limit on the suction force that the user needs to supply.

Before inhaling a new dose, it is necessary to rotate the drive wheel 53 again through one-fourth a turn in the direction 60, thereby bringing a new dose into the channel 50.

Advantageously, the channel 50 of the cassette 8 may include a constriction in the vicinity of the strip 40 so as to establish local acceleration of the sucked-through air. This local acceleration of the sucked-through air may be designed to compensate for the case where a fraction of the powder contained in the hole 41 in the strip 40 falls out of said hole 41 before being sucked up by the user: the constriction enhances entrainment of any such powder that may have fallen out from the hole. Furthermore, it is desirable for the open hole 41 to be located as close as possible inside the channel 50 to the delaminating blades 49a and 49b so as to limit any movement of the strip 40 after said hole 41 has been uncovered by delamination, thereby reducing the risk of some of the powder contained in said hole 41 falling into the channel 50.

Thus, the delaminating blades 49a and 49b may be disposed at an angle, as shown in FIG. 6c, so as to penetrate into the channel 50 of the cassette 8, converging beneath the hole 41 that is situated inside the channel 50. This disposition sets up a local constriction of said channel 50 with the advantages described above. In addition, during suction, it makes it possible to guide any powder that may have fallen out adjacent to the face 40b of the strip towards the hole 41, i.e. any powder that falls out of the side away from the suction.

In a variant, as shown in FIG. 6d, only the ends 57a and 57b of the blades 49a and 49b are curved towards the inside of the channel 50, while the portions of the blades 49a and 49b that are located in the slots 58a and 58b remain substantially parallel to the channel 50.

Furthermore, it is possible to curve the strip 40 on entering the channel 50 of the cassette so that the convex side of the strip is directed towards the mouthpiece 3, thereby causing powder to escape preferentially towards the mouthpiece 3.

As shown in FIG. 6b, the cylindrical wheel 56 on which the strip 40 is wound inside the storage housing 54 is mounted to rotate in oblong slots or in hollow oblong grooves 62 formed in the faces 45a and 45b of the cassette 8. Said oblong housings 62 extend perpendicularly to the channel 50. In addition, on one face of the cassette 8, e.g. the face 45a, a first pin 63 is disposed between the oblong housing 62 and one of the sides of the casette 8, e.g. the side 46a. Said first pin 63 extends inside the storage housing 54 over a short distance starting from the face 45a.

A second pin 64 is disposed in the vicinity of the side 46a of the cassette, likewise extending a short distance from the face 45a of the cassette. A wire-shaped metal spring 65 bears against the pins 63 and 64 so as to urge the cylindrical wheel 56 away from the channel 50 by causing said wheel to slide in the oblong housings 62.

The assembly constituted by the spring 65 and the pins 63 and 64 is narrow, thereby leaving sufficient room to receive the strip 40 wound on the wheel 56. The strip 40 may be in contact with the spring 65 and the pins 63 and 64, or else it may be separated therefrom by a protective plate 66, shown in dashed lines.

When the strip 40 is driven out from the storage housing 54 under drive from the drive wheel 53, the strip 40 wound on the cylindrical wheel 56 is unwound through a distance L, thereby causing said cylindrical wheel 56 to rotate in the direction 60. This rotary movement is braked by the resilient thrust from the spring 65 on the cylindrical wheel 56, thereby putting the strip 40 under tension. This tension is maintained after the rotary movement has come to rest. The spring 65 urges the wheel 56 away from the channel 50 and the drive wheel 53, which in the absence of the spring 65 would have the effect of unwinding the strip 40 wound on the cylindrical wheel 56. However, the friction due to the resilient pressure of the spring 65 prevents the cylindrical wheel 56 from rotating, and therefore prevents said wheel 56 from moving in the oblong holes 62. The resilient force applied by the spring 65 on the cylindrical wheel 56 is thus transmitted in full to the strip 40, thereby keeping it under tension.

Furthermore, the oblong housings 62 enable the cylindrical wheel 56 to move towards the drive wheel 53 when the tension in the strip 40 becomes too great, because rotation of said cylindrical wheel 56 has become jammed. This play allowed to the wheel 56 thus serves to prevent the strip 40 from breaking and enables the wheel 56 to be unjammed. It thus increases the reliability of the cassette 8.

However, in a variant, it is possible to provide cylindrical housings 62 forming bearings for the cylindrical wheel 56 while preventing it from moving perpendicularly to the channel 50. Under such circumstances, the tension in the strip 40 is provided solely by the friction of the spring 65 that bears resiliently against the wheel 56.

Advantageously, the cassette 8 as described above is transparent, either in full or in part, so as to enable the user to see how much strip 40 remains to be used. A portion of the strip 40 corresponding to the end of the strip may be colored so that the user is warned that the microdoses of powder stored in the cassette 8 will soon be used up. Optionally, a dose counter provided with a display may be associated with the cassette; for example, the display may indicate the number of doses that have been consumed, or the number of doses that remain to be consumed.

Figure 5A:
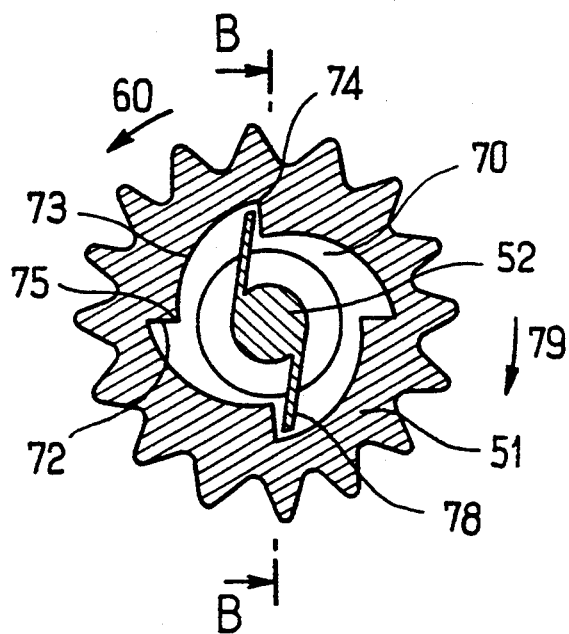
FIG. 5a is a section view on line A—A through the drive gear wheel of the cassette of FIG. 5.
Figure 5B:
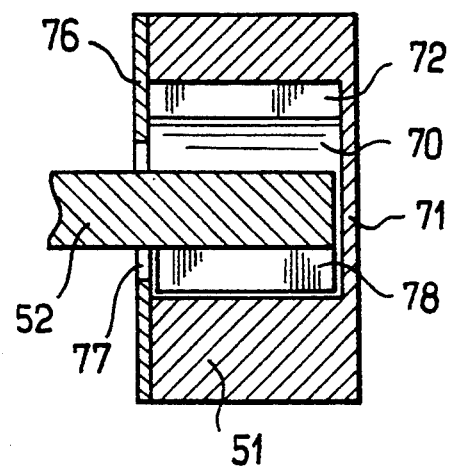

In the embodiment shown in the drawings, the gear wheel 51 is not secured to the shaft 52 and, as shown in FIGS. 5a and 5b, the gear wheel 51 may include a hollow inside 70 into which the shaft 52 penetrates. The hollow inside 70 is delimited by a solid face 71 of the gear wheel and by an inside peripheral surface of the gear wheel which is constituted by:

four radial faces 72 distributed at 90° intervals from one another, each radial face 72 including one end 74 that is relatively distant from the shaft 52 and one end 75 that is relatively close to the center of the shaft 52, with the normal to each face 72 being directed in the direction of rotation 60 about the shaft 52; and four curved surfaces 73 each joining an end 74 of a face 72 to an end 75 of another face 72.

The hollow inside 70 of the gear wheel is partially closed by means of a plate 76 pierced by a circular hole 77 allowing the shaft 52 to penetrate into said hollow inside 70 of the gear wheel.

The gear wheel 51 and the plate 77 may be made of plastic. In which case, these two pieces may be assembled together by gluing or by ultrasonic welding, for example.

Within the inside 70 of the gear wheel, the shaft 52 includes two resilient arms 78 extending in two opposite directions from the shaft 52 and substantially tangentially to said shaft 52. The length of the arms 78 is such as to enable them to extend to the ends 74 of the faces 72. In addition, the arms 78 extend in a direction such that, when the gear wheel 51 rotates in the direction 60, each arm 78 comes into abutment against a face 72 and wedges where the curved surface 73 meets the face 72, such that the shaft 52 is in turn rotated in the direction 60, thereby causing the strip 40 of microdoses to be driven by the wheel 52. In contrast, if the gear wheel 51 rotates through one-fourth of a revolution in the direction 79, each of the arms slides over a curved surface 73, deforming resiliently: the arm 78 is thus not positively entrained in the direction 79 since the torque exerted on the shaft 52 due to the resilient deformation of the arms 78 against the curved surfaces 73 is small enough to be compensated by the friction forces that act on the shaft 52. The shaft 52 is thus not rotated in the direction 79. After the gear wheel 51 has finished rotating through one-fourth of a revolution in the direction 79, the arms 78 of the shaft 52 are again to be found in the vicinity of corresponding ends 75 of faces 72 of the gear wheel, and thus ready to drive the shaft 52 next time the gear wheel is rotated in the direction 60.

The plate 77 is fixed after the shaft 52 and the arms 78 have been inserted into the hollow inside 70 of the gear wheel. Because of the plate 77, the arms 78 are thereafter held captive inside the gear wheel 51.

This free-wheel clutch device is used in the cassette 8 for the inhaler described above with reference to FIG. 1.

As shown in FIG. 3, the housing 7 for receiving the cassette 8 is provided with a recess 7a for receiving the gear wheel 51 of the cassette 8 when said cassette 8 is inserted in said housing 7.

The box 1 of the inhaler includes a well 80 extending vertically and opening out beneath the horizontal top wall 2a of the pusher 2. Said well 80 communicates with said recess 7a. Advantageously, the upper portion of the well 80 is provided with a sealing gasket 80a which prevents foreign bodies penetrating into the well 80.

The pusher 2 has a vertical rod 81 that extends vertically downwards from the horizontal top wall 2a of the pusher. The rod 81 slides through the gasket 80a and penetrates into the well 80. It includes a rack 82 suitable for meshing with the gear wheel 51 of the cassette 8 once said cassette has been inserted in the housing 7. A spring 83 is disposed around the rod 80, pressing against the box 1 and against the top wall 2a of the pusher 2.

When the mouthpiece 3 is lowered into the horizontal position, if the user presses against the pusher 2, then it moves down relative to the box 1 and the rack 82 drives the gear wheel 51 of the casette in the above-indicated direction 60.

The stroke of the pusher 2 or the length of the rack 82 is designed in association with the above-described cassette so that the gear wheel 52 rotates through one-fourth of a turn in the direction 60 for one complete stroke of said pusher 2. As described above, the shaft 52 and the drive wheel 53 of the cassette then also rotate through one-fourth of a turn in the direction 60, thereby causing the films 42 to be delaminated from the strip 40 over a length L and causing one dose of powder ready for inhaling to be inserted into the channel 50.

When the user releases the pusher 2, it is returned upwards by the spring 83.

This motion causes the gear wheel to rotate again through one-fourth of a turn, but in the direction 79, and as explained above, this movement does not cause the shaft 52 and the drive wheel of the cassette 8 to rotate because of the above-described free-wheel clutch mechanism.

A channel 84 is formed inside the box 1: it communicates firstly with the mouthpiece 3 when said mouthpiece is in its horizontal in-use position, and secondly with the housing 7 for the cassette 8. The channel 84 of the box 1 is disposed so as to be in communication with the channel 50 of the cassette 8 when said cassettes is installed in the housing 7. A non-return valve 85 is disposed inside the channel 84 in the vicinity of the mouthpiece 3.

In the embodiment shown in FIG. 3, the non-return valve 85 is in the form of a small plate, e.g. of plastic, that has its top portion rotatably received in the box 1. Thus, the valve 85 closes under gravity. If the user blows into the mouthpiece 3, then the valve 85 remains closed such that the dose of powder ready for inhaling from the cassette 8 is not in danger of being dispersed. The valve 85 could have any other known configuration without going beyond the ambit of the present invention. Optionally, the valve 85 may be returned to its closed position by resilient means such as a spring (not shown). The valve 85 may also be integrated in the mouthpiece 3. In which case, it is advantageous for the valve 85 to be integrally molded with the mouthpiece 3.

When the cassette 8 is installed in the housing 7, the channel 50 of the cassette also communicates with a channel 86 that opens out into a first cylindrical chamber 87, as shown in greater detail in FIG. 3a.

The first cylindrical chamber 87 is wider than the channel 86 so as to define a shoulder 87a. Said first cylindrical chamber 87 itself communicates with a second cylindrical chamber 88 of greater diameter than the first cylindrical chamber 87: the boundary between the first chamber 87 and the second chamber 88 thus defines a shoulder 88a. The second cylindrical chamber 88 communicates with the outside via a channel 89 that is narrower than said chamber 88. The boundary between the chamber 88 and the channel 89 thus defines a shoulder 88b. The channel 89 is advantageously fitted with filter means, such as an air filter 90, for example, which may be implemented in the form of a foam or any other porous material. The filter 90 prevents foreign bodies penetrating into the inhaler, particularly when used in a contaminated or dusty atmosphere.

A hollow piston 91 is slidably mounted in the second chamber 88. Advantageously, the piston 91 includes two peripheral sealing lips 91a and 91b disposed at respective ends thereof. The piston 91 includes a central frustoconical channel which is occupied in the rest position by a non-return valve constituted, in this case, by a frustoconical punch 92 that is complementary in shape to said frustoconical central channel in the hollow system 91. The frustoconical punch 92 is larger adjacent to the first cylindrical chamber 87, i.e. at its suction end, than it is adjacent to the channel 89. It is thus capable of lifting off the frustoconical channel of the piston 91 towards the chamber 87.

In addition, the punch 92 is narrower than the chamber 87: it can therefore penetrate into said chamber 87.

A coil spring 93 bears firstly against the shoulder 87a, and secondly against the frustoconical punch 92, urging it towards the hollow piston 91. Since the piston 91 comes into abutment against the shoulder 88b, the punch 92 is received in the frustoconical channel of said piston 91, thereby closing said channel, because of the resilient force from the spring 93. A centering pin 92a may be formed on the punch 92 so as to position the spring 93 properly relative to said punch 92.

A secondary chamber 94 opens out into the chamber 88 between the two peripheral sealing lips 91a and 91b of the piston 91 when said piston 91 is in abutment against the shoulder 88b. Said secondary channel 94 communicates with a cylindrical chamber 95 opening out to the outside of the box. The boundary between the secondary channel 94 and the chamber 95 defines a shoulder 95a. A piston 96 that extends to the outside of the box 1 by means of a rod 97 is slidably mounted in the chamber 95. The rod 97 slides in a guide 98 fixed at the outlet of the chamber 95, e.g. by being a tight fit. A coil spring 99 located inside the chamber 95 bears firstly against the guide 98 and secondly against the piston 96 so as to urge the piston towards the shoulder 95a.

At rest, the piston 96 is in abutment against the shoulder 95a, and the rod 97 does not project outside the guide 98. A hole 100, adapted to receive the rod 97 (and also visible in FIG. 2) is formed in the rear vertical wall 2b of the pusher. The hole 100 is disposed so as to be in correspondence with the rod 97 when the pusher 2 is in a high position, with no force being exerted to push the pusher 2 downwards.

Furthermore, the secondary channel 94 opens out into an upper cylindrical chamber 101 via a non-return valve 120. The upper cylindrical chamber 101 opens to the outside of the box 1 facing the top horizontal wall 2a of the pusher 2. It is downwardly delimited by a shoulder 101a. A piston 102 that includes a peripheral housing 102a in its pressure face or lower face, is slidably mounted in the cylindrical chamber 101. The piston 102 is urged upwards by a spring 105 bearing firstly against the shoulder 101a of the chamber 101 and secondly against the piston 102, in the peripheral housing 102a of said piston, in such a manner as to enable the spring 105 to be retracted into said peripheral housing 102a when the piston 102 is pushed into abutment against the shoulder 101a of the chamber 101. The piston 102 is held in the chamber 101 by snap-fastening means, e.g. such as a peripheral lip 101b which puts an upwards limit on the stroke of the piston 102. When the piston 102 is in its high position, i.e. in abutment against the peripheral lip 101b, the chamber 101 communicates with the outside via an air-vent channel 101c. The air-vent channel 101c could optionally be replaced by fluting formed inside the chamber 101, and extending a certain distance from the outlet of said chamber 101.

The piston 102 is extended upwards by a rod 103 to the vicinity of the horizontal top wall 2a of the pusher 2. The rod 103 has an enlarged top end 103a which slides in non-sealed manner in a guide 104 secured to the horizontal top wall 2a of the pusher. The guide 104 may be a tube that is substantially complementary in shape to the rod 103, or else it may be constituted by a plurality of vertical arms extending downwards from the pusher 2. In any event, the guide 104 is provided with snapfastening means 104a which may be a peripheral lip or a plurality of pins directed towards the rod 103, serving to prevent the enlarged portion 103a of said rod 103 from escaping from the guide 104. This disposition leaves a certain amount of clearance j between the enlarged portion 103a of the rod 103 and the horizontal top portion 2a of the pusher 2. This enables the rod 103 to slide inside the guide 104 over a stroke of length j.

The valve 120 allows air to pass from the chamber 101 towards the second channel 94, but not in the opposite direction. It may be implemented in various known ways. In the example shown in FIG. 3, the valve 120 conventionally comprises a gasket 106 disposed in a valve chamber in communication with the auxiliary channel 94 and the upper cylindrical chamber 101. The valve gasket 106 can take up an upper position in which it bears in sealed manner against a valve seat 107, thereby closing the valve when the pressure in the secondary channel 94 is greater than the pressure in the chamber 101. Otherwise, the valve gasket 106 takes up a lower position in which the valve is open, with communication between the secondary channel 94 and the upper chamber 101 taking place via at least one groove 108 extending from the valve seat 107 to the secondary channel 94.

Because of this mechanism, when the user actuates the pusher 2 to prepare a dose to be inhaled, by pressing, as described above, on the pusher 2, the pusher 2 begins by travelling along a stroke of length j in which the clearance j between the enlarged portion 103a of the rod 103 and the horizontal top wall 2a of the pusher 2 is taken up. During this first portion of the movement, the hole 100 moves so that it no longer faces the rod 97. Thereafter, the pusher 2 bears against the piston 102 via the rod 103. The piston 102 thus moves down inside the chamber 101 while the valve gasket 106 remains in its open, lower position. The air contained in the upper chamber 101 and the secondary channel 94 is thus compressed. This has the effect of pushing the piston 96 towards the guide 98 against the urging of the spring 99, but since the hole 100 of the pusher is no longer facing the rod 97, the rod comes into abutment against the rear vertical wall of said pusher 2.

Since the secondary channel 94 opens out into the chamber 88 between the peripheral sealing lips 91a and 91b of the piston 91, this compression of the air does not cause the piston 91 to move, nor does it cause the frustoconical valve member 92 to move. Advantageously, as shown in FIG. 3a, the sealing lips 91a and 91b of the piston may point slightly towards the channel 94 so that their sealing is reinforced when the pressure in said channel 94 increases.

So long as the user presses against the pusher 2, the pusher remains in a lowered position such that the hole 100 of the pusher does not face the rod 97 of the piston 96. The stroke of the piston 96 is thus limited by abutment of the rod 97 against the vertical rear wall 2b of the pusher.

When the user releases the pusher 2, said pusher returns to its rest position under drive from the spring 83. As a result, the piston 102 rises in the chamber 101. It may be observed that the piston 83 could optionally be omitted, with the action of the tube 104 and of the lip 104a sufficing to raise the piston. In a variant, the tube 104 could optionally be omitted, providing the piston 102 is sufficiently well guided inside the chamber 101, in which case the spring suffices to raise the piston 102.

Because of the drop in pressure that results from the piston 102 rising in the chamber 101, the valve gasket 106 bears against the valve seat 107 under the effect of the higher pressure in the secondary channel 94, thereby isolating the secondary channel 94 in which the pressure is maintained. When the piston 102 reaches its high position, the chamber 101 is put into communication with the outside via the air vent channel 101c. The piston 96 thus continues to be urged towards the guide 98. Since the hole 100 of the pusher 2 is now in correspondence with the rod 97, the piston 96 compresses the spring 98 causing the rod 97 to engage in the hole 100.

Thus, once the user has actuated the pusher on one occasion and a dose of powder is ready to be inhaled inside the channel 50 of the cassette 8, the pusher 2 is locked by the rod 97 engaging in the hole 100 of the pusher 2. It is thus not possible to operate the inhaler wrongly by actuating the pusher several times before inhaling any powder.

In addition, the user can easily see that the inhaler is "armed", i.e. that a dose of powder has been prepared by actuating the pusher 2, merely by looking to see whether or not the rod 97 is engaged in the hole 100 of the pusher 2. This observation may be facilitated by making the rod 97 of a color that is different from that of the pusher 2.

Once the inhaler has been "armed", the user can inhale the dose of powder prepared in the channel 50 of the cassette 8 by moving the mouthpiece 3 into its horizontal position, by putting it into the mouth, and by sucking.

The intake of air opens the valve 85 and initially displaces the hollow piston 91 together with the punch 92 towards the chamber 87, until said hollow piston 91 comes into abutment against the shoulder 88a of said chamber 88, after which the frustoconical punch 92 is disconnected from said piston 91 with the punch 92 moving into the chamber 87 against the resilient force of the spring 93. At this point, a flow of air generated by the suction can now pass through the air filter 90 into the channel 89, into the chamber 88, along the central channel of the piston 91 from which the frustoconical punch 92 has been removed, into the chamber 87 around said frustoconical punch 92, into the chamber 86, along the channel 50 of the cassette 8, and in particular through the hole 41 of the strip 40 containing the dose of powder to be inhaled, into the channel 84, into the mouthpiece 3, into the mouth, and finally through the respiratory tracts into the lungs, thereby entraining the dose of powder contained in the channel 50 of the cassette 8.

In a variant, the central channel of the piston 91 may be cylindrical in shape and provided with longitudinal fluting, and the punch 92 may be a cylindrical part slidably received in the channel of the piston 91. In which case, the punch 92 must include an enlarged head adjacent to the chamber 87, said head being adapted to bear against the piston 91 while providing peripheral sealing around the central channel of the piston 91 under urging from the spring 93, and said head must also be adapted to enter the chamber 87 while the user is providing suction. The passage of air between the piston 91 and the punch 92 then takes place along the longitudinal fluting of the central channel of the piston 91.

Simultaneously, during said suction and until it comes into abutment against the shoulder 88a, the translation motion of the piston 91 puts the secondary channel 94 into communication with the outside. The pressure in the channel 94 then comes into balance with atmospheric pressure, thus enabling the spring 99 to push the piston 96 until it comes into abutment against the shoulder 95a. The rod 97 then returns into the guide 98, and the pusher 2 is no longer locked; the valve gasket 106 moves back down into its open position.

Furthermore, at the end of air intake by the user, the spring 93 pushes the frustoconical punch 92 back into the hollow channel of the piston 91, urging the piston 91 into abutment against the shoulder 88b. The inhaler has thus been returned to its starting position ready for reuse. The mouthpiece 3 can then be put into its vertical position to lock the inhaler prior to subsequent use.

FIG. 14 shows a particularly advantageous variant of the device shown in FIGS. 3 and 3a, where the cylindrical second chamber 88 communicates with the air inlet channel 89 via a non-return valve 890. The valve 890 communicates with the chamber 88 via an orifice 890c which is narrower than said chamber 88, thereby defining the shoulder 88b of said chamber 88.

The valve 890 closes when greater pressure occurs in the chamber 88 and it opens when said greater pressure ceases. The valve 890 may have any conventional form: in the particular example shown in FIG. 14, it comprises a flexible gasket 890a which is larger than the orifice 890c and which is adapted to bear in sealed manner against a valve seat 890b, thereby closing the channel 89 when higher pressure occurs in the chamber 88. When the higher pressure in the chamber 88 ceases, the gasket 890a lifts off the seat 890b. In this position, communication between the chamber 88 and the channel 89 is provided via at least one groove 890d extending between the orifice 890c and the valve seat 890b, or by any other equivalent means. Apart from the presence of the valve 890, the device is similar to that shown in FIGS. 3 and 3a, with the same references designating portions that are identical or similar.

In the variant of FIG. 14, when the user sucks air through the suction channel after arming the device, the piston 91 and the punch 92 move together towards the chamber 87 as described above. The translation motion of the piston 91 puts the secondary channel 94 containing compressed air into communication with the chamber 88. The pressure of the air in the chamber 88 therefore increases, which has the effect firstly of closing the valve 890 and secondly of assisting user suction in displacing the hollow piston 91 and the frustoconical punch 92 together until contact is made with the shoulder 88a, and thus in overcoming friction between the piston 91 and the chamber 88 and in overcoming the resilient force of the spring 93, after which it helps in disconnecting the punch 92 from the hollow piston 91, with said punch 92 being moved into the chamber 87 against the resilient force of the spring 93. The compressed air in the secondary channel 94 then escapes towards the channel 86 and the suction channel, and begins to entrain the dose of powder prepared by actuating the pusher 2.

This assistance in sucking up the dose of powder provided by the compressed air initially contained in the secondary channel 94 is particularly advantageous when the inhaler is for use with patients suffering from reduced respiratory capacity.

Clearly the box 1 as shown in FIGS. 3, 3a, and 14 cannot be made as a single piece, because of its complex shape. It may possibly be built up from two longitudinal halves that are separated by a vertical plane and which are subsequently assembled together, e.g. by ultrasonic welding. The box 1 may also include a larger number of assembled-together parts. Such variants are not described in detail herein, and form part of the common knowledge of the person skilled in the art.

FIGS. 15, 15a, and 16 show a variant of the FIG. 6 cassette which is adapted to facilitate delamination of the films 42 and the strip 40. In this variant, the cassette includes, in the housings 58a and 58b for recovering the delaminated films 42, two respective spools 52a and 52b onto which the delaminated films 42 are wound. The spools 52a and 52b are each rotated in one direction simultaneously with the drive wheel 53 being rotated. Because they are so thin, winding up the films 42 on the spools 52a and 52b does not significantly change the diameter of said spools 52a and 52b, and therefore does not significantly change the length of film wound up for a given angular displacement of the spools 52a and 52b. The films 42 may be fixed to the spools 52a and 52b by any conventional means. For example, as shown diagrammatically in FIG. 16, each of the spools 52a and 52b may include a substantially radial slot 520 in its periphery, with the films 42 being inserted in respective ones of said slots 52 while being installed in the cassette. Thereafter, the films 42 are driven by friction against the spools 52a and 52b, on each occasion that the drive wheel 53 is actuated. In a variant, the ends of the films 42 may also be glued to the spools 52a and 52b.

As a result, the films 42 are delaminated by traction from the spools 52a and 52b, either on its own or in combination with the action of the delaminating blades 49a and 49b.

In this embodiment, the delaminating blades 49a and 49b may optionally be omitted, in which case they may be replaced merely by a slot having substantially the same thickness as the strip 40, so as to provide sealing for the channel 50 in the casette. However, the delaminating blades 49a and 49b may also be retained in order to combine the effect thereof with that of the spools 52a and 52b.

The spools 52a and 52b may be connected to respective external gear wheels 51a and 51b situated on the same face of the cassette as the gear wheel 51 for the drive wheel. Advantageously, one of the two gear wheels 51a and 51b is disposed so as to be in alignment with the gear wheel 51, parallel to the rectilinear sides 46a and 46b of the cassette.

Figure 17:
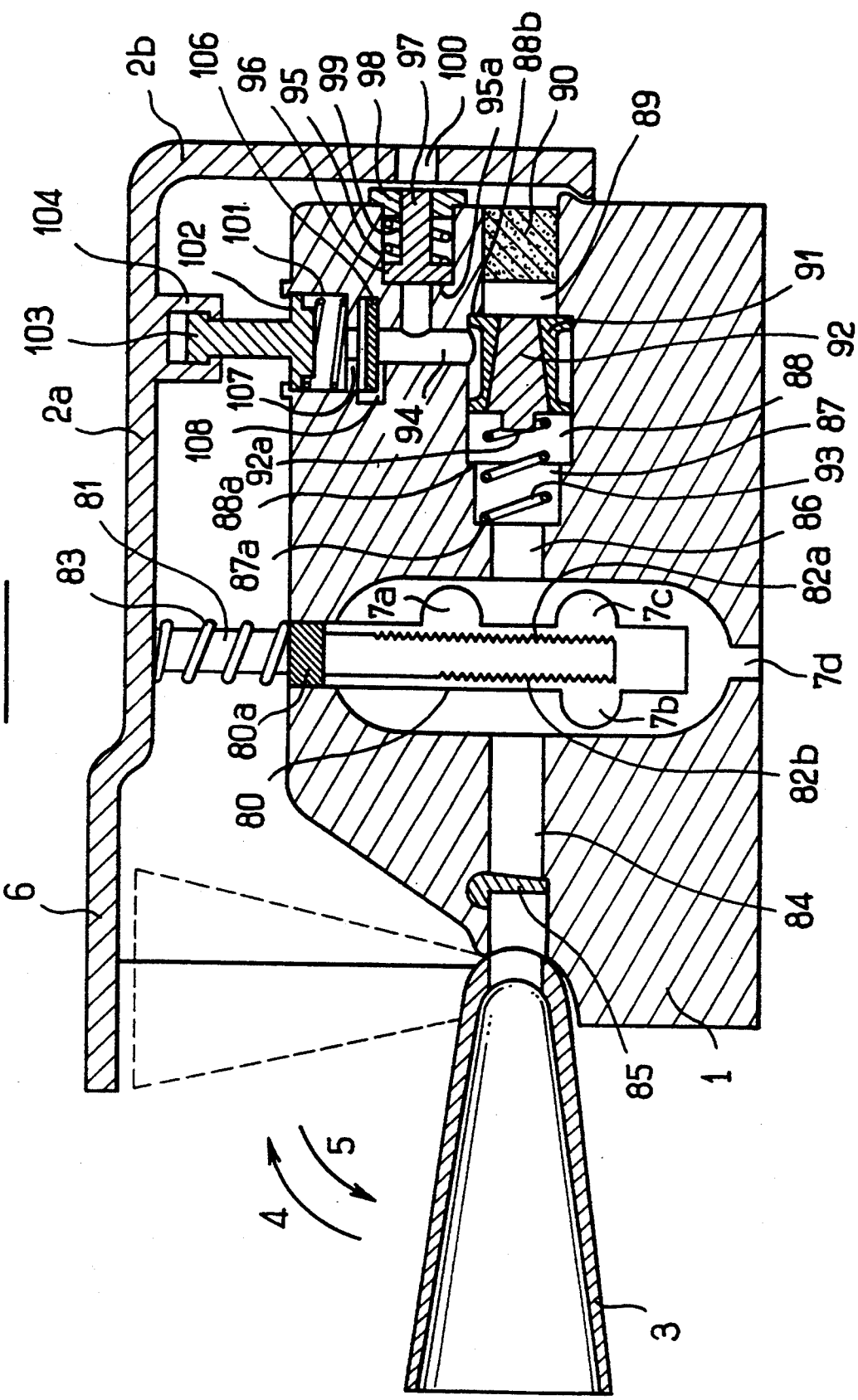
FIG. 17 is a view similar to FIG. 3, for a variant inhaler in accordance with the invention and adapted to use the cassette of FIG. 15.

The cassette of FIGS. 15 to 16 can thus be used in an inhaler as shown in FIG. 17, which inhaler is very similar in design to that shown in FIG. 3, but has a rod 81 provided with two racks 82a and 82b. The rack 82a is adapted to mesh with the gear wheels 51 and 51a, while the rack 82b is adapted to mesh with the gear wheel 51b. In addition to the recess 7a for receiving the gear wheel 51, the box has a recess 7b for receiving the gear wheel 51b and a recess 7c for receiving the gear wheel 51a when the cassettes 8 of FIGS. 15 to 16 is inserted in the housing 7 of said box.

In order to ensure that each of the spools 52a and 52b is driven in one direction of rotation only, they are linked to their respective gear wheels 51a and 51b via free-wheel mechanisms similar to that shown in FIGS. 5a and 5b. Given the configuration of the cassette shown in FIGS. 15 to 16 and of the inhaler shown in FIG. 17, it will be observed that the free-wheel mechanisms of all three gear wheels 51, 51a, and 51b must be such that the corresponding drive wheels are driven solely when the rod 81 moves down inside the well 80, i.e. when the user presses on the pusher 2.

In FIG. 17, the box 1 of the inhaler includes a slot 7d which puts a bottom portion of the housing 7 that receives the cassette 8 into communication with the outside. Thus, when a transparent cassette is installed in the housing 7, the user can observe one of the faces of the strip 40 wound inside the storage housing 54. Numerals indicating the number of doses that remain or the number of doses that have been consumed may thus be marked on the strip 40 and observed by the user through the slot 7d. In a variant, or in addition to numerical markings, the end of the strip 40 may be colored in distinctive manner, so as to warn the user that the cassette will shortly be used up.

If the volume of each microdose of powder is too large, it is less advantageous to store the microdoses in a strip 40 wound up inside a cassette 8, mainly because of the size of the resulting cassette. It is then necessary to use an inhaler that has a tank of powder.

The inhaler shown in FIG. 9 has numerous portions in common with the inhaler described above. The common portions are not described again: only the novel portions are described.

The box 1 does not have a recess 7, and the channel 4 opens out directly into above-described chamber 87. The channel 84 also communicates via a short channel 84a with a recess 210 in the box that opens out in the vicinity of the horizontal top wall 2a of the pusher 2. The housing 210 contains a tank 200 of powder constituted by an outer enclosure 201 containing an inner tank 202 that is filled with powder. The inner tank 202 slides vertically with lost motion inside the outer enclosure 201.

The outer enclosure 201 is shown in detail in FIG. 9a. It comprises a peripheral side wall 201a, a horizontal top wall 201b, and a horizontal bottom wall 201d. The top wall 201b is generally in the form of an add-on piece fixed to the peripheral side wall 201a by any conventional means, e.g. by ultrasonic welding, after the inner tank 202 has been installed inside the enclosure 201. Said top wall 201b includes a central orifice 201c, and said horizontal bottom wall 201d includes a central orifice 201e that flares towards the inside of the enclosure 201 and that is extended downwards by a short tubular portion 201f.

The enclosure 201 defines an inside chamber 201g of height h1. The enclosure 201 is of a shape adapted to engage in the housing 210 of the box 1, such that the tubular portion 201f lies close to the channel 84 and above said channel 84, as shown in FIG. 9.

As shown in detail in FIG. 9b, the inner tank 202 has a peripheral side wall 202a, a horizontal top wall 202b, and a horizontal bottom wall 202c.

The peripheral side wall 202a is adapted to slide vertically in the inside chamber 201g of the enclosure 201. As for the enclosure 201, the horizontal top wall 202b is generally an add-on piece, being secured to the side wall 202a by any conventional means. The height of the side wall 202a plus the thickness of the horizontal wall 202b comes to a height h2 that is less than h1. The horizontal wall 202b includes an internal top tubular portion 202d adapted to slide in the orifice 201c in the top of the enclosure 201. The bottom horizontal wall 202c includes a flared bottom portion 202e which is substantially complementary in shape to the inside shape of the flared orifice 201e of the enclosure 201. The flared portion 202e extends downward in the form of a bottom tubular portion 202f adapted to slide inside the tubular portion 201f of the enclosure 201 and in the channel 84a of the box 1. The bottom tubular portion 202f is in vertical alignment with the top tubular portion 202d.

As shown in FIG. 9, the inner tank 202 is filled with powder and is placed inside the enclosure 201 which is itself engaged in the housing 210 of the box 1. A conical resilient ring 203 is disposed between the horizontal bottom wall 201d of the enclosure 201 and the bottom wall 202c of the inner tank 202. This resilient ring urges the inner tank 202 upwards, and at rest it presses the top wall 202b of the tank 202 into abutment against the top wall 201b of the enclosure 201.

With reference to FIG. 9, the rod 81 of the pusher 2 (already described with reference to FIG. 3) slides in the top tubular portion 202d and in the bottom tubular portion 202f of the inner tank 202.

The rod 81 further includes a thin peripheral clip 205 situated immediately above the top tubular portion 202d of the inner tank 202 when the rod 84 is in its rest position.

Conventionally, the clip 205 may be a separate part received in a peripheral groove in the rod 81. The clip 205 may alternatively be constituted by a simple projection formed on the rod 81 during molding: in which case, the projection need not be peripheral.

Said rod 84 is pierced by a hole 204 extending parallel to the channel 84, the hole 204 may optionally be flared towards the mouthpiece 3. At rest, the hole 204 lies inside the internal tank 202 containing the powder. The inside volume of the hole 204 corresponds to the volume of one dose of powder. Unlike the inhaler shown in FIG. 2, the rod 81 does not include a rack.

In addition, the channel 84 includes a bottom recess 206 in line with the rod 81. A flap 207 is pivotally mounted about an axis 208 that extends horizontally and perpendicularly to the channel 84, being situated in the bottom of the channel 84. A first portion 207a of the flap 207 is capable of pivoting into the recess 206, while another portion 207b secured to the first portion 207a of the flap 207 pivots within the channel 84. At rest, the first portion 207a of the flap 207 isolates the lower recess 206: the flap 207 may be held in this position by resilient means such as a return spring for the second portion 207b of the flap or a spring urging the first portion 207a of said flap into the closed position, or else the flap 207 may be held in this position by giving the second portion 207b of the flap a mass that is greater than that of the first portion 207a.

When the user presses on the pusher 2, the rod 81 moves down inside the box 1. Because of the presence of the clip 205 which comes into abutment against the top tubular portion 202d of the inner tank 202, the rod 81 begins by entraining the tank 202 in its displacement. The tank 202 thus slides down inside the enclosure 201 against the thrust of the conical resilient ring 203.

When the thrust of said conical resilient ring 203 becomes too strong, or when the inner tank 202 comes into abutment against the bottom wall 201d of the enclosure 201, the clip 205 is retracted by compression and slides into the top tubular portion 202d of the inner tank 202, while simultaneously the rod 81 moves down through said inner tank 202. During this movement, the inner tank 202 is thrust violently upwards by the conical resilient ring 203: this provides shaking that contributes to ensuring that the hole 204 of the rod 81 is properly filled with powder, in particular by expelling any air that might be trapped in said hole 204, and replacing the air with powder. Advantageously, this shock takes place when the hole 204 is in the flared portion 202e of the inner tank 202, thereby making it possible to use up substantially all of the powder contained in the inner tank 202, with said powder being guided into the hole 204 by the flared portion 202e.

The downwards movement of the rod 81 continues until it penetrates into the recess 206 causing the flap 207 to pivot about its axis 208. Because the clip 205 retracts suddenly, this downwards movement of the rod 81 is very quick. The portion 207a of the flap 207 is thus thrust suddenly into the recess 206, and the portion 207b of the flap 207 is thrust suddenly against the hole 204 of the rod 81 on the side thereof distant from the mouthpiece 3, and while travelling towards the mouthpiece 3. This jolt propels the dose of powder contained in the hole 204 a short distance towards the mouthpiece 3. The dose of powder initially contained in the hole 204 thus falls into the channel 84, between the mouthpiece 3 and the recess 206.

When the user releases the pusher 2, it is returned upwards by the spring 83 described above with reference to FIG. 3, thereby entraining the rod 81 which releases the recess 206, and the flap 207 recloses the recess 206, thereby preventing the powder contained in the channel 84 falling into said recess 206. The thrust from the spring 83 must be sufficient to cause the clip 205 to pass back above the top tubular portion 202d of the inner tank 202.

The pusher 2 is then locked by the rod 97 in the manner explained above. When the user sucks up the dose of powder contained in the channel 84, the pusher 2 is unlocked in the same manner as explained above.

Another embodiment of the inhaler having a tank is shown in FIG. 10.

In this embodiment, as in the embodiment of FIG. 9, the channel 84 communicates directly with the chamber 87. In addition, the rod 81 is extended vertically downwards by a narrow flexible tongue 300. The rod 81 slides in sealed manner in a well 301 which extends to the channel 84 and which then continues in the form of a guide channel 302 in which the tongue 300 slides in sealed manner. The length of the tongue 300 is such that it never escapes completely from the guide channel 302: thus, a bottom portion 300a of the tongue 300 always remains in the guide channel 302 when the rod 81 is in its raised position.

The guide channel 302 includes a vertical portion 302a beneath the channel 84 followed by a curved portion 302b which is extended by a horizontal portion 302c. Above the horizontal portion 302e of the guide channel 302, there is a tank 303 filled with the powder to be inhaled. The tank 303 flares upwards and it includes an outlet orifice 304 in its bottom portion which opens out into the horizontal portion 302c of the channel 302.

At rest, the orifice 304 is closed by a slide 305 which slides in the horizontal portion 302c of the guide channel 302. The slide 305 is urged towards its closed position by a spring 306 disposed in said horizontal portion 302c of the guide channel 302.

The flexible tongue 300 is pierced by a hole 307 parallel to the channel 84, which hole may be cylindrical or conical, in which case it flares towards the mouthpiece 3. At rest, the hole 307 lies inside the channel 84. The inside volume of the hole 307 corresponds to the volume of a dose of powder that is to be inhaled. When the user presses on the pusher 2, the rod 81 moves down in the well 301 and the tongue 300 moves down in the guide channel 302. The flexibility of the tongue 300 enables it to follow the curved portion 302b of the guide 302 and then to push back the slide 305 against the resilient urging of the spring 306 until the hole 307 lies under the outlet orifice 304 of the tank 303. The hole 307 then fills with powder. Advantageously, the inhaler includes means enabling a jolt to be imparted to the box 1 while the hole is being filled with powder, as for the embodiment of FIG. 9.

When the user releases the pusher 2, it moves back up to its rest position under drive from the spring 83 as described above with reference to FIG. 3. The hole 307 filled with powder, thus moves back into the channel 84, and the pusher 2 is locked as explained above.

The user can then suck up a dose of powder contained in the hole 307 of the tongue 300, thereby unlocking the pusher 2, in the manner explained above.

FIG. 11 shows a third embodiment of the tank inhaler, in which a thin circular wheel 400 having four sawtooth-shaped peripheral notches 101 at 90° intervals is rotatably mounted in a circular housing 402 in the box 1. The housing 402 is of substantially the same diameter and the same thickness as the wheel 400. The notches 401 are isolated by the wheel 400 making sealing contact with the housing 402. Such sealing may be obtained, for example, by a peripheral sealing lip 401c, as shown in FIG. 11b.

As shown in FIG. 11a, the wheel 400 is secured to a shaft 452 which penetrates into a hollow gear wheel 451 analogous to the above-described gear wheel 51 of the cassette 8. Inside the gear wheel 451, the shaft 452 has two resilient arms analogous to the above-described resilient arms 78 on the shaft 52 of the cassette 8.

The shaft 452 and the gear wheel 451 thus co-operate to form a free-wheel mechanism whereby the gear wheel 451 drives the shaft 452 and the wheel 400 in rotation in a direction 410 when said gear wheel 451 rotates in said direction 410, while said gear wheel does not drive the shaft 452 and the wheel 400 when it rotates in the direction opposite to the direction 410.

With reference to FIG. 11, the gear wheel 451 engages a rack 82 of above-described rod 81. The rod 81 slides vertically in a well 480 in the box 1 when the pusher 2 is actuated. The well 480 may optionally include a sealing gasket in the top portion thereof, as in the embodiment of FIG. 3.

When the rod 81 moves downwards, the gear wheel 451 rotates through one-fourth a turn in the direction 410, and as a result the wheel 400 also rotates through one-fourth of a turn in the direction 410. When the rod 81 moves upwards, the gear wheel 451 again rotates through one-fourth of a turn, this time in the direction opposite to the direction 410, but the wheel 400 remains stationary since the gear wheel 410 does not drive the shaft 452 in the direction opposite to the direction 410.

The box 1 includes a channel 84 which connects the mouthpiece 3 as described above with reference to FIG. 3 to the chamber 87 as described with reference to FIG. 3a. The channel 84 includes a non-return valve 85 as described with reference to FIG. 3, and situated in the vicinity of the mouthpiece 3.

The housing 402 is situated above the channel 84 and it communicates with said channel 84 so that a bottom portion of the wheel 400 penetrates into the channel 84. In addition, the notches 401 and the wheel 400 are disposed in such a manner that after each occasion on which the pusher 2 has been actuated to cause the wheel 400 to rotate in the direction 410, a first notch 401 occupies a bottom first position 420 and penetrates into the channel 84 substantially beneath the shaft 452. Since the notches 401 are disposed at 90° intervals to one another, a second notch 401 lies in a second position 430 substantially level with the shaft 452 adjacent to the mouthpiece 3, a third notch 401 occupies a third position 440 substantially above the shaft 452, and a fourth notch 401 occupies a fourth position 450 at substantially the same level as the shaft 452, and adjacent to the chamber 87.

In FIG. 11, said second notch 401 in the position 430 penetrates into a tank 403 formed in the box and filled with powder to be inhaled. The tank 403 may flare upwards so as to encourage the powder to move downwards towards said second notch 401 as the tank 403 is emptied. Advantageously, each of the notches 401 includes a radial first face 401a whose normal extends in the direction of rotation 410, and a second face 401b substantially perpendicular to the first.

Thus, when the user presses down the pusher 2, the rod 81 moves down into its well 480, thereby rotating the gear wheel 451 through one-fourth of a turn in the direction 410 under drive from the rack 82. The gear wheel 451 thus rotates the shaft 452 and the wheel 400 in the direction 410 through one-fourth of a turn. During this movement, said second notch which was initially in the position 430 passes from the tank 403 into the housing 402, taking with it a volume of powder that corresponds to one dose of powder to be inhaled. Because of the sealing lip 401c, the powder entrained by said second notch is held captive in said second notch.

At the end of the rotation through one-fourth of a turn, the notch 401 that was initially in the position 430 lies in said position 440, substantially above the shaft 452, and full of powder. The notch that was initially in the position 440 and which would normally itself have been filled with powder, is now to be found in said position 450. The notch 401 that was initially in the position 450 and which was likewise normally filled with powder is now to be found in the position 410, i.e. in the channel 84. The powder it contained therefore falls into said channel 84. Finally, the notch 401 which was initially in the position 420 is now in the position 430 inside the tank of powder 403.

When the user releases the pusher 2, it moves back up under drive from the spring 83 as described with reference to FIG. 3, and the rod 81 rotates the gear wheel 451 through one-fourth of a turn in the direction opposite to the direction 410. As already mentioned, this does not cause the wheel 400 to rotate.

Once the pusher 2 has returned to its rest position, it is locked by the same mechanism as in the embodiment of FIG. 3.

The user can then inhale the powder that has fallen into the channel 84, thereby unlocking the pusher 2 in the same manner as with the embodiment of FIG. 3.

This embodiment of the inhaler of the invention has been described with a tank 403 of powder disposed so that said second notch situated at exactly the same level as the shaft 452 on the mouthpiece side thereof penetrates into said tank 403. However, the tank 403 could be located elsewhere without going beyond the scope of the present invention. In particular, it could be disposed as shown in FIG. 12 in said fourth position 450 again substantially at the same level as the shaft 452, but this time on the same side as the chamber 87. In this case, the power taken from the tank 403 in said position 450 passes directly into the channel 84 when the wheel 400 rotates through one-quarter of a turn in the direction 410. The notches 401 in the positions 420, 430, and 440 then contain no powder at all. Furthermore, in this variant embodiment, filling of the notches as they pass through the tank 403 is facilitated by the fact that the powder falls naturally under gravity into said notches.

In the embodiments of FIGS. 11 and 12, the inhaler may include means enabling a jolt to be imparted to the box 1 each time powder is filled into a notch, as in the embodiment of FIG. 9.

In the embodiments of FIGS. 11 and 12, the wheel 400 may rotate in the direction opposite to the direction 410, providing the orientation of the notches 401 is inverted, so that the normals to the faces 401a remain oriented in the direction of rotation of the wheel 400.

In all of the embodiments of the inhaler described above, inhaling of the powder may be improved by placing at least two screw portions 501, 502 as shown in FIG. 13 in the channel 84. The two screw portions 501 and 502 are disposed so as to establish discontinuity in the flow of air containing the powder so as to break up any agglomerations of powder that may exist and thus facilitate good mixing of the powder in the sucked-in flow of air.

Discontinuity may be obtained by using two screw portions 501, 502 having the same pitch, each occupying substantially half a helical revolution, but with said portions being angularly offset, about a common longitudinal axis, e.g. by 90°.

A grid may optionally be added to the screw portions 501 and 502 in order to finish off the breaking-up effect. The grid may optionally replace the screw portions 501 and 502.

We claim:

1. A powder inhaler, comprising: a box (1), a suction channel (84) formed in said box for enabling a user to inhale powder, a powder stored in a supply (54, 202, 303, 403) containing a plurality of doses of said powder, a pusher (2) for use prior to inhaling to displace a dose of powder from said supply of powder into the suction channel (84), locking mechanism means included in the box for locking the pusher after it has been actuated, said locking mechanism means including means (91, 92, 93) responsive to user suction in the suction channel for releasing said locking mechanism when a pressure reduction is established in the suction channel by user suction, thereby enabling said pusher to be actuated again before a next user inhalation, and return spring means (83) associated with the pusher to return the pusher to a rest position thereof.

2. A powder inhaler according to claim 1, in which the locking mechanism is pneumatic, means (102,120) being provided for establishing pneumatic pressure by actuating the pusher (2), the locking mechanism means including a latch (97) actuatable by said pressure, and said means (91, 92, 93) responsive to suction being adapted to eliminate said pressure Under the effect of suction created in the suction channel (84) so as to unlock said latch (97).

3. A powder inhaler according to claim 2, wherein said locking mechanism compresses:

- a first piston (102) actuated by the pusher (2), said piston sliding in a first cylindrical chamber (101) containing air, in such a manner as to compress the air when the pusher (2) is moved towards the box (1) after the pusher has travelled through a certain stroke (j), said first cylindrical chamber (101) communicating with the outside via an air vent channel (101*c*) when the first piston (102) is in a rest position;
- a secondary channel (94) communicating with said first cylindrical chamber (101) via a first non-return valve (120) enabling the air contained in said first cylindrical chamber (101) to pass into said secondary channel (94), but not the other way;
- a second cylindrical chamber (95) opening out into the vicinity of a side wall (2*b*) of the pusher (2) and communicating with said secondary channel (94);
- a second piston (96) sliding in said second cylindrical chamber (95), said second piston (96) being extended towards said side wall (2*b*) of the pusher (2) by a rod (97);
- spring means (99) disposed in said second cylindrical chamber (95) urging said second piston (96) towards said secondary channel (94);
- a housing (100) in said side wall (2*b*) of the pusher (2), adapted to receive the rod (97) of said second piston (96) when the pusher (2) is in a rest position after actuation of said pusher (2) has compressed the air contained in the secondary channel (94) by the action of the first piston (102) and of the first non-return valve (106), thereby having the effect of pushing said second piston (96) and its rod (97) towards said side wall (2*b*) of the pusher (2);
- a third cylindrical chamber (88) extending said suction channel (84), said third cylindrical chamber being disposed between said suction channel (84) and an air inlet channel (89) opening to the outside of the box (1), said third cylindrical chamber (88) communicating with the secondary channel (94);
- a fourth cylindrical chamber (87) extending said third cylindrical chamber (88) towards the suction channel (84), being of diameter smaller than the diameter of said third cylindrical chamber (88), and being separated from said third cylindrical chamber (88) by a shoulder (88*a*);
- a hollow piston (91) sliding in said third cylindrical chamber (88); and
- a second non-return valve (92) of a size suitable for entering into said fourth cylindrical chamber (87), being disposed between said suction channel (84) and said hollow piston (91), said second valve being biased by spring means (93) to close said third cylindrical chamber (88) and to push said hollow piston (91) into a position where it interrupts communication between said secondary channel (94) and said third cylindrical chamber (88), the fourth of said spring means (93) being small enough for suction established by a user in the suction channel (84) initially to displace said hollow piston (91) and said second valve (92) against the bias of the spring (93), and secondly to disconnect said second valve (92) from said hollow piston (91), entraining said second valve (92) into said fourth cylindrical chamber (87), while the hollow piston (91) remains in abutment against said shoulder (88*a*) separating said third cylindrical chamber (88) from said fourth cylindrical chamber (87).

4. An inhaler according to claim 3, wherein the first piston (102) is connected with lost motion to the pusher (2) having clearance equal to said stroke (j) after which said pusher (2) actuates said first piston (102) in such a manner that the pusher (2) returns said first piston (102) into its rest position when said pusher (2) itself returns to its rest position.

5. An inhaler according to claim 3, wherein the first piston (102) is urged towards the pusher (2) by spring means (105) and said first cylindrical chamber (101) includes abutment means preventing said first piston (102) from leaving said first cylindrical chamber (101) under the effect of said spring means (105).

6. An inhaler according to claim 3, wherein the air inlet channel (89) includes an air filter (90).

7. A powder inhaler according to claim 3, further comprises a third non-return valve (890) disposed between the third cylindrical chamber (88) and the air inlet channel (89), said third valve (890) being adapted to close when higher pressure is created in said third cylindrical chamber (88) and to open when the higher pressure in said third cylindrical chamber (88) ceases.

8. An inhaler according to claim 3, in which said locking means include signalling means (97) indicating whether the pusher (2) is locked or unlocked, and said signalling means (97) is constituted by the rod (97) of the second piston (96), and the housing (100) formed in the side wall (2b) of the pusher is a hole passing through said side wall, in such a manner that said rod (97) can be seen, at least when it penetrates into said hole.

9. A powder inhaler according to claim 1, wherein said suction channel (84) includes a suction valve (85) enabling the user to suck air via the suction channel (84), but preventing the user from blowing air into said suction channel (84).

10. A powder inhaler according to claim 1, in which the suction channel (89) is outwardly extended by a tubular mouthpiece (3) mounted rotatably so as to be capable, selectively, of being placed in an in-use first position in which it communicates with said suction channel (84), or in a storage. Second position in which said mouthpiece (3) engages beneath a portion (6) of the pusher (2) in such a manner as to lock it.

11. An inhaler according to claim 1, wherein said suction channel (84) includes powder break-up means (501, 502).

12. An inhaler according to claim 11, wherein said powder break up means (501, 502) include at least two screw portions (501, 502) that are angularly offset about a common longitudinal axis so as to establish discontinuity in the flow of air sucked in by the user.

13. A powder inhaler according to claim 1, wherein the box (1) includes a housing (7) for receiving a removable cassette (8) containing doses of powder to be inhaled, said cassette (8) itself including a channel (50) extending the suction channel (84) when the cassette (8) is inserted in the housing (7) of the box (1).

14. An inhaler according to clam 13, wherein said cassette (8) contains a flexible strip (40) carrying said doses of powder to be inhaled, and said cassette includes strip drive means (51, 52, 53) which, when the cassette (8) is installed in the box (1) are mechanically engaged with drive means (81, 82) driven by the pusher (2) so as to expose in the channel (50) of the cassette, a portion of the strip (4) carrying a new dose of said powder, each time the pusher (2) is actuated.

15. An inhaler according to claim 14, wherein said strip has two faces (40a, 40b) and holes (41) opening out into both faces (40a, 40b) and distributed along the length of said strip, each of said holes (41) being filled with a dose of powder to be inhaled, each of the two faces (40a, 40b) of the strip including an adhesive protective film (42) closing said holes (41), said strip drive means (51, 52, 53) being disposed on one side of the cassette channel (50) and driving the strip (4) by traction, the strip (40) passing through the cassette channel (50) while occupying a plane that is substantially perpendicular to said channel (50), the cassette including delamination means (49a, 49b; 52a, 52b) disposed relative to the cassette channel (50) opposite to the strip drive means (53), said delamination means being adapted to remove said protective films (42) from the strip (40) before the strip penetrates into the channel (50) of the cassette.

16. An inhaler according to claim 15, wherein said adhesive films include adhesive-free zones (25) facing the holes (41) in the strip (40).

17. An inhaler according to claim 15, further characterized in that the holes (41) in the strip (40) are frustoconial, flaring towards said suction channel (84).

18. An inhaler according to claim 14, wherein said actuator means (81, 82) driven by the pusher (2) comprise a rod (81) secured to the pusher and provided with at least one rack (82), said strip drive means (51, 52, 53) including a drive wheel (53) rotated by a gear wheel (51) that meshes with the rack (82), said drive wheel (53) being connected to the gear wheel (51) by a freewheel mechanism (72, 73, 78) enabling the gear wheel to drive said drive wheel when said gear wheel rotates in a preferred direction of rotation, but not driving the drive wheel when said gear wheel rotates in the opposite direction.

19. An inhaler according to claim 15, wherein the means for delaminating the cassette strip (40) comprises two spools (52a, 52b) onto which the two films (42) of the strip are wound respectively, each of the protective film wind-up spools (52a, 52b) being rotated by a respective gear wheel (51a, 51b) that meshes with at least one rack (82a, 82b) of the rod (81) secured to the pusher, and the protective film wind-up spools (52a, 52b) are connected to their respective gear wheels (51a, 51b) via a freewheel mechanism, (72, 73, 78) enabling each gear wheel to drive the corresponding wind-up spool when said gear wheel rotates in a preferred direction of rotation, but not driving the wind-up spool when the gear wheel rotates in the opposite direction.

20. An inhaler according to claim 14, wherein said delamination means include two blades (49a, 49b) each applied against one of the faces of the strip (40).

21. An inhaler according to claims 1, wherein the box (1) includes a tank (200) containing powder to be inhaled, the pusher (2) including a rod (81) pierced by a hole (204) parallel to the suction channel (84) and sliding between a raised first position in which the hole (204) slides inside the tank (200), and a lowered second position in which the hole (204) through the rod lies in said suction channel (84), and the box (1) further includes means (207) for ejecting the dose of powder to cause the dose of powder contained in the hole (204) of the rod (81) to be ejected therefrom when said rod is in its lowered position.

22. An inhaler according to claim 21, wherein the ejection means (207) is a flap mounted to pivot about an axis (208), said flap (207) comprising two portions (207a, 207b) on either side of the axis (208), a first portion (207a) for pivoting into a recess (206) communicating with said suction channel (84) when the rod (81) of the pusher (2) reaches its lowered position, while the second portion (207b) of the flap strikes an end of the hole (204) of the rod (81), thereby projecting the dose of powder contained in said hole (204) out from said hole (204) into the suction channel (84).

23. An inhaler according to claim 22, wherein said first portion (207a) of said flap (207) isolates said recess (206) that communicates with said suction channel (84) when said pusher (2) is in its raised position.

24. An inhaler according to claim 21, wherein the tank (200) of powder comprises an inner tank (202) containing the powder and through which the rod (81)

of the pusher (2) slides, said inner tank (202) being slideable with lost motion inside an enclosure (201) secured to the box (1), said inner tank (202) being urged towards the pusher (2) by resilient means (203), and in that the rod (81) includes external extension means (205) suitable for driving the inner tank (202) against the bias of the resilient means (203) when the rod (81) is pushed into the box (1), and then to retract to enable the rod (81) to slide through the inner tank (202) once the bias of the resilient means (203) reaches a limit value or once said inner tank (202) reaches an abutment position.

25. An inhaler according to claim 21, wherein the tank including the powder includes at least one upwardly flared bottom portion (202e).

26. An inhaler according to claim 1, wherein the pusher (2) includes a rod (81) sliding inside a well (301) of the box (1) between a raised first position and a lowered second position, said well (301) communicating with the suction channel (84), the rod (81) being extended by a flexible tongue (300), pierced by a hole (307) having an inside volume equal to the volume of one dose of powder, said hole (307) being parallel to the suction channel (84) and lying in said suction channel (84) when the pusher (2) is in its raised position, the box (1) including a guide channel (302) for the flexible tongue (300) communicating with said suction channel, including a vertical portion (302a) in line with said flexible tongue (300), a curved portion (302b), and then a horizontal portion (302c) situation beneath a tank (303) of powder and communicating with said tank (303) via an opening (304), said opening (304) being capable of being closed by a slider (305) sliding in said bottom portion (302c) of said guide channel (302), said slider (305) being biased by a spring (306) towards a position in which it closes the opening (304) of the tank (303), the flexible tongue (300) being adapted to push the slider (305) against the bias of the spring (306) so as to bring the hole (307) of said tongue beneath the opening (304) of the tank (303) when the pusher (2) is in its lowered position.

27. An inhaler according to claim 26, wherein a bottom portion (300a) of the tongue (300) remains in said guide channel (302) when the rod (81) is in its raised position.

28. An inhaler according to claim 26, wherein said tank (303) includes at least a bottom portion that is upwardly flared.

29. An inhaler according to claim 1, wherein the pusher (2) includes a rod (81) sliding in a well (480) of the box (1) and provided with a rack (82), the box (1) including a wheel (400) rotatably mounted in a substantially circular housing (402), said rod (81) including regularly spaced apart peripheral notches (401) each of inside volume equal to the volume of a dose to be inhaled, said wheel (400) being provided with a shaft (452) linked to a gear wheel (451) by a free-wheel mechanism (72, 73, 78) such that when the gear wheel (451) rotates in a preferred direction of rotation (410) it drives the wheel (400), but when it rotates in the opposite direction, the wheel (400) is not driven, the gear wheel (451) meshing with the rack (82) of the rod (81) of the pusher, the box (1) including the tank (403) into which the wheel (400) penetrates so as to fill the notches (401) with powder, the wheel (400) penetrating into the suction channel (84), and the notches (401) being disposed in such a manner that a new notch (401) penetrates into the suction channel (84) each time the pusher (2) is actuated, thereby bringing a new dose of powder into said suction channel (84).

30. An inhaler according to claim 29, wherein each of said notches (401) includes a radial face (401a) having a normal that is directed in the preferred direction of rotation (410), and a face (401b) perpendicular to said radial face (401).

31. An inhaler according to claim 29, wherein said tank (403) includes at least an upwardly flared bottom portion.

32. An inhaler according to claim 29, wherein said notches (401) are provided with peripheral sealing lips (401c) which bear resiliently against said substantially circular housing (402) when said notches (401) are within said housing (402).

33. An inhaler according to claim 1, in which said locking means include signalling means (97) indicating whether the pusher (2) is locked or unlocked.

34. A powder inhaler, comprising: a box (1), a suction channel (84) formed in said box for enabling a user to inhale powder, a powder being stored in a supply containing a plurality of doses of said powder, a pusher (2) for use prior to inhaling to displace a dose of powder from said supply of powder into the suction channel, said supply including a tank (200) containing powder to be inhaled, the pusher (2) including a rod (81) pierced by a hole (204) parallel to the suction channel (84) and sliding between a raised first position in which the hole (204) slides inside the tank (200), and a lowered second position in which the hole (204) through the rod lies in said suction channel (84), and the tank (200) of powder comprising an inner tank (202) containing the powder and through which the rod (81) of the pusher (2) slides, said inner tank (202) sliding with lost motion inside an enclosure (201) secured to the box (1), said inner tank (202) being urged towards the pusher (2) by resilient means (203), and the rod (81) including external extension means (205) suitable for driving the inner tank (202) against the bias of the resilient means (203) when the rod (81) is pushed into the box (1), and then to retract to enable the rod (81) to slide through the inner tank (202) once the bias of the resilient means (203) reaches a limit value or once said inner tank (202) reaches an abutment position.

35. A powder inhaler as claimed in claim 34, in which the box (1) further includes means (207) for ejecting the dose of powder to cause the dose of powder contained in the hole (204) of the rod (81) to be ejected therefrom when said rod is in its lowered position.

36. A powder inhaler, comprising: a box (1), a channel (84) formed in said box for enabling a user to inhale powder, a powder stored in a supply containing a plurality of doses of said powder, a pusher (2) for use prior to inhaling to displace a dose of powder from said supply of powder into the channel, said supply including a tank containing powder to be inhaled, the pusher (2) being connected to a metering member having a recess movable between a first position where it communicates with the tank to receive said dose of powder and a second position where it communicates with the channel to displace said dose of powder from said tank into said channel, means for imparting a jolt to said box for accurately filling said recess with said dose of powder when the recess is in its first position, and locking mechanism means included in the box for locking the pusher after it has been actuated, said locking mechanism means including means (91, 92, 93) responsive to user suction in the channel for releasing said locking mechanism when a pressure reduction is established in the channel by user suction, thereby enabling said pusher to be actuated again before a next user inhalation.

* * * * *